(12) United States Patent
Lewis

(10) Patent No.: US 10,961,480 B2
(45) Date of Patent: Mar. 30, 2021

(54) HIGH STABILITY LUBRICATING OIL BASE STOCKS AND PROCESSES FOR PREPARING THE SAME

(71) Applicant: ExxonMobil Chemical Patents Inc., Baytown, TX (US)

(72) Inventor: Kyle G. Lewis, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 143 days.

(21) Appl. No.: 15/854,948

(22) Filed: Dec. 27, 2017

(65) Prior Publication Data

US 2018/0201858 A1 Jul. 19, 2018

Related U.S. Application Data

(60) Provisional application No. 62/446,943, filed on Jan. 17, 2017.

(51) Int. Cl.
*C10M 105/72* (2006.01)
*C07C 321/28* (2006.01)
(Continued)

(52) U.S. Cl.
CPC ......... *C10M 105/72* (2013.01); *C07C 319/18* (2013.01); *C07C 321/14* (2013.01);
(Continued)

(58) Field of Classification Search
CPC .......... C10M 105/72; C10M 2219/086; C10M 2219/082; C07C 321/28; C07C 319/18;
(Continued)

(56) References Cited

U.S. PATENT DOCUMENTS 2,051,807 A * 8/1936 Allen ...................... C07C 2/868
568/59
3,084,196 A 4/1963 Laufer
(Continued)

FOREIGN PATENT DOCUMENTS

JP H8-283233 10/1996

OTHER PUBLICATIONS

U.S. Appl. No. 62/523,398, filed Jun. 22, 2017 Oumar-Mahamat et al.
(Continued)

*Primary Examiner* — Cephia D Toomer

(57) ABSTRACT

Compounds having the formula (F-I) below are provided herein:

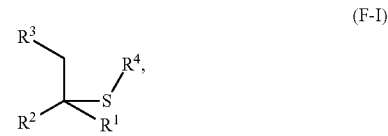

(F-I)

wherein: $R^1$ is a $C_1$-$C_{5000}$ alkyl group; $R^2$ is (i) a $C_4$-$C_{30}$ linear alkyl group or (ii) a $C_4$-$C_{5000}$ branched alkyl having the formula (F-II) below:

(F-II)

(Continued)

wherein $R^5$ and $R^6$ at each occurrence are each independently a hydrogen or a $C_1$-$C_{30}$ linear alkyl group and n is a positive integer, provided however, among all of $R^5$ and $R^6$, at least one is a $C_1$-$C_{30}$ linear alkyl group; and $R^7$ is a hydrogen or a $C_1$-$C_{30}$ linear alkyl group; $R^3$ is hydrogen or a $C_1$-$C_{5000}$ alkyl group; and $R^4$ is a $C_1$-$C_{50}$ alkyl group or an aromatic group. Processes for preparing compounds of formula (F-I) as well as base stock and lubricant compositions containing compounds of formula (F-I) are also provided.

30 Claims, 6 Drawing Sheets

(51) Int. Cl.

| | |
|---|---|
| C07C 319/18 | (2006.01) |
| C07C 321/14 | (2006.01) |
| C10N 20/02 | (2006.01) |
| C10N 20/00 | (2006.01) |
| C10N 30/08 | (2006.01) |
| C10N 30/10 | (2006.01) |
| C10N 30/00 | (2006.01) |

(52) U.S. Cl.
CPC ..... *C07C 321/28* (2013.01); *C10M 2219/082* (2013.01); *C10M 2219/086* (2013.01); *C10N 2020/011* (2020.05); *C10N 2020/02* (2013.01); *C10N 2030/08* (2013.01); *C10N 2030/10* (2013.01); *C10N 2030/74* (2020.05)

(58) Field of Classification Search
CPC .............. C07C 321/14; C10N 2230/10; C10N 2230/08; C10N 2220/022; C10N 2220/023; C10N 2230/74
USPC .............................. 568/21, 38; 508/567, 569
See application file for complete search history.

(56) References Cited

U.S. PATENT DOCUMENTS

| | | | |
|---|---|---|---|
| 4,820,756 A | 4/1989 | Pittelout et al. | |
| 4,929,732 A | 5/1990 | Meier et al. | |
| 6,329,395 B1 | 12/2001 | Sundeep et al. | |
| 6,645,920 B1 * | 11/2003 | Butke .................. | C10M 141/08 508/282 |
| 9,133,411 B2 | 9/2015 | Patil et al. | |
| 9,243,201 B2 | 1/2016 | Patil et al. | |
| 9,422,498 B2 | 8/2016 | Patil et al. | |
| 9,422,499 B2 | 8/2016 | Patil et al. | |
| 9,422,502 B2 | 8/2016 | Patil et al. | |
| 9,458,403 B2 | 10/2016 | Patil et al. | |
| 9,719,041 B2 | 8/2017 | Patil et al. | |
| 2013/0109604 A1 | 5/2013 | Onkar et al. | |
| 2014/0121143 A1 | 5/2014 | Patil et al. | |
| 2015/0275117 A1 | 10/2015 | Patil et al. | |
| 2015/0275129 A1 | 10/2015 | Patil et al. | |
| 2015/0275728 A1 | 10/2015 | Braun et al. | |
| 2016/0033170 A1 | 2/2016 | Urbanski | |
| 2016/0138863 A1 | 5/2016 | Urbanski | |
| 2017/0183595 A1 | 6/2017 | Ng et al. | |

OTHER PUBLICATIONS

Casals et al., "Chimie Macromoleculaire," Compte Rendus des Seances de L'Academie des Sciences, Serie C: Sciences Chimiques, Elsevier France, Editioins Scientifiques et Medicales, FR, Jan. 1, 1972, vol. 274, pp. 1039-1042.

NCBI:"SCHEMBL12898156-C10H22S-PubChem" (Feb. 13, 2015) retrieved from https://pubchem.ncbi.nlm.nih.gov/compound/88976273#section=Top.
NCBI:"CID91112627-C11H24S-PubChem" (Mar. 17, 2015) retrieved from https://pubchem.ncbi.nlm.nih.gov/compound/91112627#section=Top.
NCBI:"CID91188713-C11H24S-PubChem" (Mar. 17, 2015) retrieved from https://pubchem.ncbi.nlm.nih.gov/compound/91188713#section=Top.
NCBI:"Bis(1-ethyl-1,5-dirnethylhexyl) suifide-C20H142S-PubChem" (2015-12-18) retrieved from https://pubchem.ncbi.nlm.nih.gov/compound/101745905#section=Top.
Barton, D. et al, "Some Further Novel Transformations of Germinal (pyridine-2-thiyl) Phenylsulphones", Tetrahedron Letters, vol. 30, No. 32, pp. 4237-4240, 1989.
Cain, M.E. et al., "Reversible Formation and Solvolysis of Tertiary Alkyl Sulphides in Acetic Acid-Perchloric Acid" Journal of the Chemical Society, pp. 1694-1699, 1962.
Barton, D., et al., "The invention of New Radical Chain Reactions. Part 11. New Method of the Generation of Tertiary Radicals from Tertiary Alcohols" Journal of the Chemical Society, Perkin Transactions 1, pp. 1603-1612, 1986.
De Graaf, W., "Low-temperature Addition of Hydrogen Polysuifides to Olefins: Formation of 2,2'-dialkyl Polysulfides and Alk-1-enes and cyclic (poly) sulfides and polymeric organic sulfur compounds from [alpha], [omega]-dienes", Journal of the Chemical Society, Perkin Transactions 1, vol. 6, pp. 635-640, 1995.
Choy, N., et al. "Simplified Discoderrnolide Analogues: Synthesis and Biological Evaluation of 4-e pi-7-Dehydroxy-14, 16-didernethyl-(+)-discodermolides as Microtubule-Stabilizing Agents", Journal of Medicinal Chemistry, vol. 46, No. 14, pp. 2846-2864, 2003.
Gurijavallabhan, V., et al. "Regioselective Cobalt-Catalyzed Addition of Sulfides to Unactivated Alkenes", The Journal of Organic Chemistry, vol. 76, No. 15, pp. 6442-6446, 2001.
Jean, M. et al. "Gold-catalyzed C-S Bond formation form thiols" Tetrahedron Letters, vol. 51, No. 2, pp. 378-381, 2010.
Polster, J., et al. "Structure-Odor Correlations in Homologous Series of Alkanethiols and Attempts to Predict Odor Thresholds by 3D-QSAR Studies", Journal of Agricultural and Food Chemistry, vol. 63, No, 5; pp. 1419-1432, 2015.
Li, Z., et al. "Tribological Study of Hydrolytically Stable S-Containing Alkyl Phenylboric Esters as Lubricant Additives.", Royal Society of Chemistry, vol. 4, No. 48, pp. 25118-25126, 2014.
Pohmakotr, M., et al. "[alpha]-Arylsufanyl-[alpha]fluoro Carbenoids: Their Novel Chemistry and Synthetic Applications", Organic Letters, vol. 24, pp. 4547-4550, 2004.
Kohnen, M. et al. "Sulphur-bound Steroid and Phytane Carbon Skeletons in Geomacromoiecules: Implications for the Mechanism of Incorporation of Sulphur into Organic Matter", Geochimica et Cosmochimica Acta., vol. 57, No. 11, pp. 2515-2528, 1993.
NCBI:"SCHEMBL16899603-C16H34S-PubChem" (Feb. 23, 2016) retrieved from https://pubchem.ncbi.nlm.nih.gov/compound/118227067#section=Top.
NCBI:"CID19838532" (Dec. 5, 2017) retrieved from https://pubchem.ncbi.nlm.nih.gov/compound/19838532#section=Top.
NCBI:"SCHEMBL10079038-C18H30S-PubChem" (Nov. 30, 2012) retrieved from https://pubchem.ncbi.nlm.nih.gov/compound/68028721#section=Top.
NCBI:"SCHEMBL3263818-C30H62S-PubChem" (Feb. 12, 2015) retrieved from https://pubchem.ncbi.nlm.nih.gov/compound/87501544#section=Top.
NCBI:"SCHEMBL10079628-C24H50S-PubChem" (Feb. 13, 2015) retrieved from https://pubchem.ncbi.nlm.nih.gov/compound/88563526#section=Top.
NCBI:"SCHEMBL12017237-C13H28S-PubChem" (Feb. 13, 2015) retrieved from https://pubchem.ncbi.nlm.nih.gov/compound/88869550#section=Top.

* cited by examiner

HIGH STABILITY LUBRICATING OIL BASE STOCKS AND PROCESSES FOR PREPARING THE SAME

PRIORITY CLAIM

This application claims the benefit of Provisional Application No. 62/446,943, filed Jan. 17, 2017, the disclosures of which is incorporated herein by its reference.

FIELD OF THE INVENTION

This disclosure relates to sulfur-containing compounds, processes for producing the sulfur-containing compounds, and lubricating oil base stocks and lubricating oils including the sulfur-containing compounds with increased thermal and oxidative stability.

BACKGROUND OF THE INVENTION

Lubricants in commercial use today are prepared from a variety of natural and synthetic base stocks admixed with various additive packages and solvents depending upon their intended application. The base stocks typically include mineral oils, polyalpha-olefins (PAO), gas-to-liquid base oils (GTL), silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks.

PAOs and GTL stocks are an important class of lube base stocks with many excellent lubricating properties, including high viscosity index (VI), but may have lower thermal and oxidative stability. Thermal and oxidative stability is important because of a trend requiring smaller sump sizes that may result in more thermal and oxidative stress on the lubricants. Further, performance requirements for lubricants have become more stringent and the demand for longer drain intervals continues to grow.

Sulfur may be incorporated in the base stocks due to its anti-oxidant capabilities. While sulfurized PAO (S-PAO) base stocks can provide improved oxidative stability, improved durability during exposure to high temperatures and overall may extend the life of the lubricant, synthesis of S-PAO bases tocks may introduce a tertiary C—H bond in addition to the sulfur atom. For example, as shown in known scheme A below, under radical initiated conditions, where R may be an alkyl

Scheme A

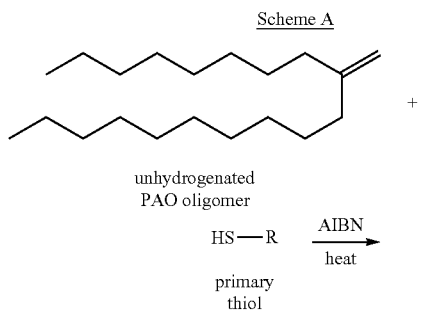

unhydrogenated PAO oligomer $$HS-R \xrightarrow{\text{AIBN}}_{\text{heat}}$$

primary thiol

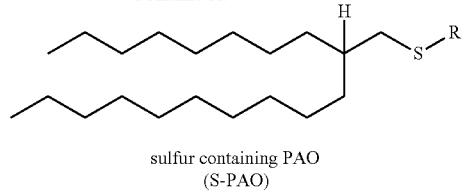

sulfur containing PAO (S-PAO)

group or aromatic compound, the sulfur addition follows the well-known "anti-Markovnikov addition," wherein the sulfur atom bonds to the less substituted carbon atom of the double bond from the unhydrogenated PAO oligomer forming a tertiary C—H bond in the S-PAO. This hydrogen atom of the C—H bond may be particularly labile to oxidative cleavage due to low tertiary C—H bond dissociation energy. Thus, such tertiary C—H bond can be prone to oxidative degradation thereby lowering the oxidative stability of the S-PAO.

Therefore, there is a need for S-PAOs with increased thermal and oxidative stability and processes for making S-PAOs, which do not introduce oxidatively labile tertiary C—H bonds. More specifically, there is a need for S-PAOs and methods of preparing the same where the sulfur atom bonds to the more highly substituted carbon atom of the double bond from the unhydrogenated PAO oligomer.

SUMMARY OF THE INVENTION

It has been unexpectedly found that higher stability S-PAOs may be selectively synthesized without introducing oxidatively labile tertiary C—H bonds via acid catalyzed synthesis.

Thus, this disclosure relates in part to a lubricant base stock comprising a compound having the formula (F-I) below:

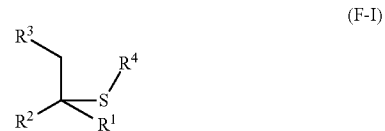

(F-I)

wherein: $R^1$ is a $C_1$-$C_{5000}$ alkyl group; $R^2$ is (i) a $C_4$-$C_{30}$ linear alkyl group or (ii) a $C_4$-$C_{5000}$ branched alkyl group having the formula (F-II) below:

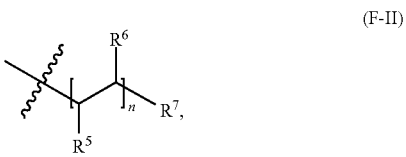

(F-II)

wherein $R^5$ and $R^6$ at each occurrence are each independently a hydrogen or a $C_1$-$C_{30}$ linear alkyl group and n is a positive integer, provided however, among all of $R^5$ and $R^6$, at least one is a $C_1$-$C_{30}$ linear alkyl group; and $R^7$ is a hydrogen or a $C_1$-$C_{30}$ linear alkyl group; $R^3$ is hydrogen or a $C_1$-$C_{500}$ alkyl group; and $R^4$ is a $C_1$-$C_{50}$ alkyl group or an aromatic group.

This disclosure also relates in part to a process for making a compound of formula (F-I) and/or a base stock comprising a compound of formula (F-I), the process comprising reacting HS-R$^4$ with an olefin-containing material comprising a compound having the following formula:

in the presence of an acid catalyst.

This disclosure further relates in part to a formulated lubricant comprising one or more of the lubricant base stocks described herein.

Other embodiments, including particular aspects of the embodiments summarized above, will be evident from the detailed description that follows.

DETAILED DESCRIPTION OF THE INVENTION

Figure 1:
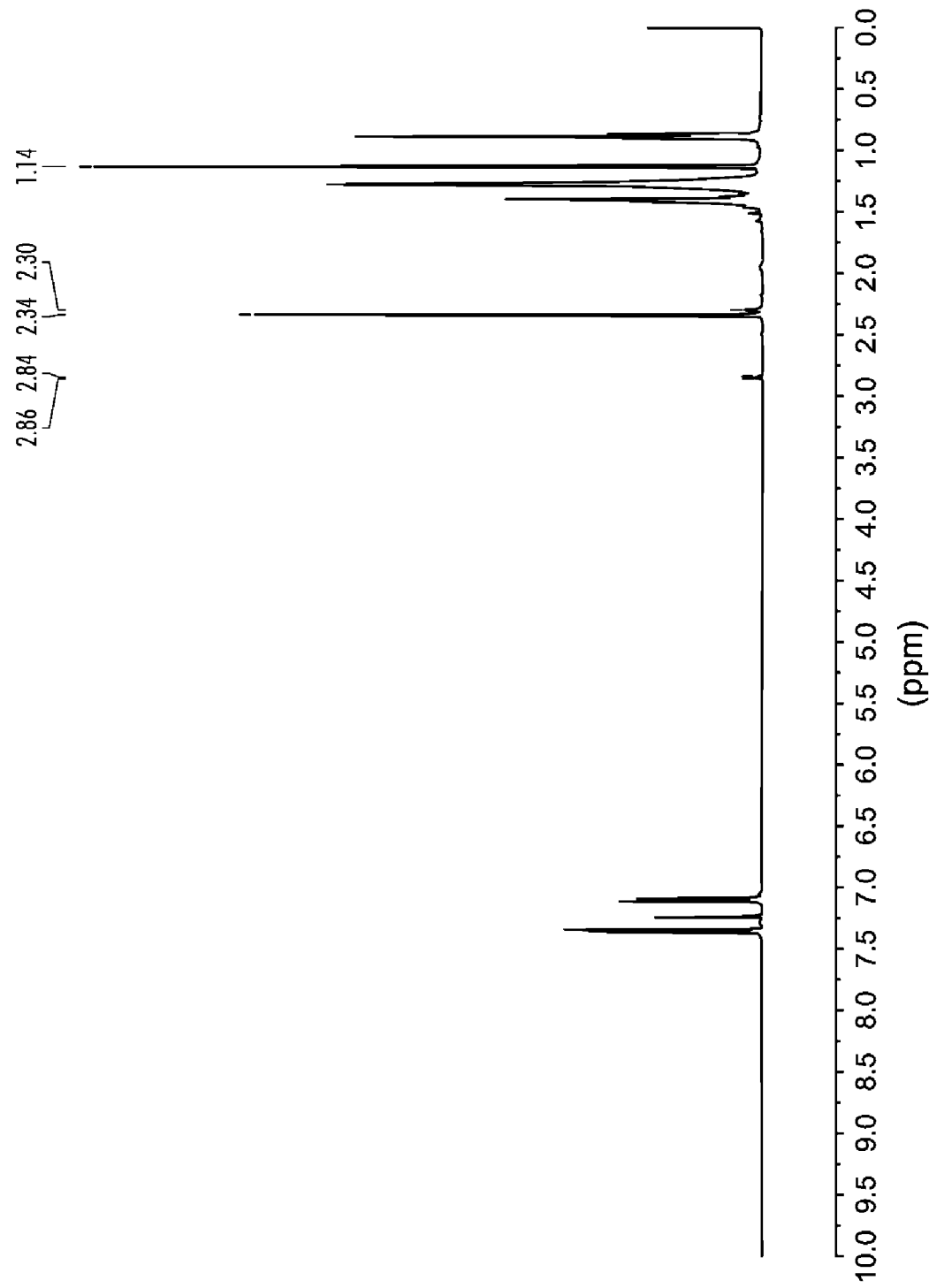
FIG. 1 illustrates $^1$H NMR spectra of Product I.

In various aspects of the invention, catalysts and methods for preparing catalysts are provided.

I. Definitions

For purposes of this invention and the claims hereto, the numbering scheme for the Periodic Table Groups is according to the IUPAC Periodic Table of Elements as of Jan. 1, 2017.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 1000 carbon atoms (i.e. $C_1$-$C_{1000}$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and isopropyl, and "$C_4$ alkyl" refers to the butyl groups (e.g. —$CH_2CH_2CH_2CH_3$, —CH($CH_3$)$CH_2CH_3$, —$CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "aromatic" refers to unsaturated hydrocarbons comprising an aromatic ring in structures thereof, the aromatic ring having a delocalized conjugated π system and preferably having from 4 to 20 carbon atoms. Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. The aromatic may optionally be substituted, e.g., with one or more alkyl group, alkoxy group, halogen, etc.

The aromatic ring may comprise one or more heteroatoms. Examples of heteroatoms include, but are not limited to, nitrogen, oxygen, and/or sulfur. Aromatics with one or more heteroatom in the aromatic ring therein include, but are not limited to furan, benzofuran, thiophene, benzothiophene, oxazole, thiazole and the like, and combinations thereof. The aromatic ring may be monocyclic, bicyclic, tricyclic, and/or polycyclic (in some embodiments, at least monocyclic rings, only monocyclic and bicyclic rings, or only monocyclic rings) and may be fused rings.

As used herein, the term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be straight-chain, branched-chain or cyclic. "Olefin" is intended to embrace all structural isomeric forms of olefins, unless it is specified to mean a single isomer or the context clearly indicates otherwise.

As used herein, the term "alpha-olefin" refer to an olefin having a terminal carbon-to-carbon double bond (($R_1R_2$)—C=$CH_2$) in the structure thereof.

As used herein, "polyalpha-olefin(s)" ("PAO(s)") includes any oligomer(s) and polymer(s) of one or more alpha-olefin monomer(s). Thus, the PAO can be a dimer, a trimer, a tetramer, or any other oligomer or polymer comprising two or more structure units derived from one or more alpha-olefin monomer(s). The PAO molecule can be highly regio-regular, such that the bulk material exhibits an isotacticity, or a syndiotacticity when measured by $^{13}$C NMR. The PAO molecule can be highly regio-irregular, such that the bulk material is substantially atactic when measured by $^{13}$C NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO").

A PAO molecule as obtained from the polymerization or oligomerization of alpha-olefin monomers, without further hydrogenation thereof, typically contains an ethylenically unsaturated C=C double bond in the structure thereof. An unhydrogenated PAO is sometimes referred to as a "uPAO" herein. A uPAO material could comprise, among others, vinyls (F-A below, where R is an alkyl), 2,2-di-substituted olefins (F-B below, also-known-as vinylidenes, where R1 and R2, the same or different, are alkyls), 1,2-di-substituted olefins (including the E- and Z-isomers of F-C1 and F-C2 below, also-known-as di-substituted vinylenes, where $R_1$ and $R_2$, the same or different, are alkyls), and tri-substituted olefins (F-D below, also-known-as tri-substituted vinylenes, where $R_1$, $R_2$, and $R_3$, the same or different, are alkyls). The vinyls and vinylidenes are terminal olefins, while the di- and tri-substituted vinylene olefins are internal olefins.

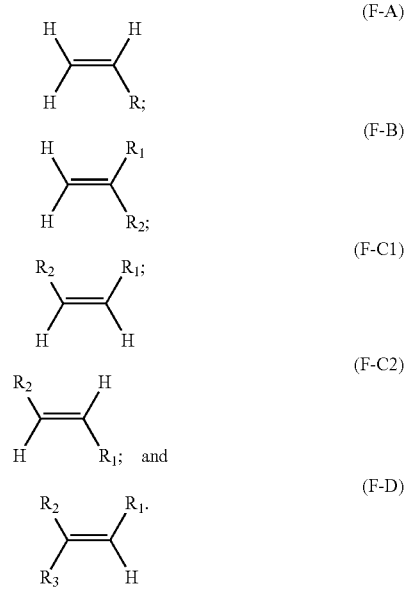

Group II, Group III, Group IV, Group V and Group VI base stocks. PAOs, particularly hydrogenated PAOs, have recently found wide use in lubricant formulations as a Group IV base stock.

NMR spectroscopy provides key structural information about the synthesized polymers. Proton NMR ($^1$H-NMR) analysis of the uPAO gives a quantitative breakdown of the olefinic structure types (viz. vinyls, 1,2-di-substituted vinylenes, tri-substituted vinylenes, and vinylidenes). In the present disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least a 500 MHz is run under the following conditions: a 30° flip angle RF pulse, 120 scans, with a delay of 5 seconds between pulses; sample dissolved in $CDCl_3$ (deuterated chloroform); and signal collection temperature at 25° C. The following approach is taken in determining the concentrations of the various olefins among all of the olefins from an NMR graph. First, peaks corresponding to different types of hydrogen atoms in vinyls (T1), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, $Ci=100*Qi/Qt$).

TABLE I

| Hydrogen Atoms | | Peak Region (ppm) | Peak Area | Number of Hydrogen Atoms | Quantity of Olefin (mol) | Concentration of Olefin (mol %) |
| --- | --- | --- | --- | --- | --- | --- |
| Type No. | Olefin Structure | | | | | |
| T1 | $CH_2=CH-R_1$ | 4.95-5.10 | A1 | 2 | Q1 = A1/2 | C1 |
| T2 | $CH_2=CR_1R_2$ | 4.70-4.84 | A2 | 2 | Q2 = A2/2 | C2 |
| T3 | $CHR_1=CHR_2$ | 5.31-5.55 | A3 | 2 | Q3 = A3/2 | C3 |
| T4 | $CR_1R_2=CHR_3$ | 5.11-5.30 | A4 | 1 | Q4 = A4 | C4 |

A uPAO can be hydrogenated in the presence of hydrogen and a hydrogenation catalyst to reduce the ethylenic unsaturation thereof and obtain a hydrogenated PAO. Such hydrogenated PAO can be more stable compared to the corresponding uPAO, offering higher thermal and oxidative resistance. A uPAO can be otherwise chemically modified to obtain a derivative thereof given the chemical reactivity of the ethylenic C=C double bond therein. The derivative can offer various interesting physical and chemical properties depending on the functional group attached to the carbon chain as a result of the modification.

As used herein, the term "lubricant" refers to a substance that can be introduced between two or more moving surfaces and lowers the level of friction between two adjacent surfaces moving relative to each other. A lubricant "base stock" is a material, typically a fluid at the operating temperature of the lubricant, used to formulate a lubricant by admixing with other components. Non-limiting examples of base stocks suitable in lubricants include API Group I, Carbon-13 NMR ($^{13}$C-NMR) is used to determine tacticity of the PAOs of the present invention. Carbon-13 NMR can be used to determine the concentration of the triads, denoted (m,m)-triads (i.e., meso, meso), (m,r)- (i.e., meso, racemic) and (r,r)- (i.e., racemic, racemic) triads, respectively. The concentrations of these triads defines whether the polymer is isotactic, atactic or syndiotactic. In the present disclosure, the concentration of the (m,m)-triads in mol % is recorded as the isotacticity of the PAO material. Spectra for a PAO sample are acquired in the following manner. Approximately 100-1000 mg of the PAO sample is dissolved in 2-3 ml of chloroform-d for $^{13}$C-NMR analysis. The samples are run with a 60 second delay and 90° pulse with at least 512 transients. The tacticity was calculated using the peak around 35 ppm ($CH_2$ peak next to the branch point). Analysis of the spectra is performed according to the paper by Kim, I.; Zhou, J.-M.; and Chung, H. Journal of Polymer Science: Part A: Polymer Chemistry 2000, 38 1687-1697. The calculation of tacticity is mm*100/(mm+mr+rr) for the molar percentages of (m,m)-triads, mr*100/(mm+mr+rr) for the molar percentages of (m,r)-triads, and rr*100/(mm+mr+rr) for the molar percentages of (r,r)-triads. The (m,m)-triads correspond to 35.5-34.55 ppm, the (m,r)-triads to 34.55-34.1 ppm, and the (r,r)-triads to 34.1-33.2 ppm.

II. Sulfur-Containing Compounds Useful for Base Stocks

The present disclosure relates to sulfur-containing compounds, which are useful in base stock compositions due to their increased thermal and oxidative stability. In particular, sulfur-containing compounds are provided herein, which can be selectively synthesized from an unhydrogenated PAO (uPAO) and a thiol compound with an acid catalyst such that the sulfur atom bonds predominantly to the more highly substituted carbon atom of the double bond in the uPAO instead of the sulfur atom bonding to the less substituted carbon to avoid formation of an oxidatively labile tertiary C—H bond. Thus, compounds having the formula (F-I) below are provided herein:

(F-I)

wherein:
$R^1$ is a $C_1$-$C_{5000}$ alkyl group;
$R^2$ is (i) a $C_4$-$C_{30}$ linear alkyl group or (ii) a $C_4$-$C_{5000}$ branched alkyl having the formula (F-II) below:

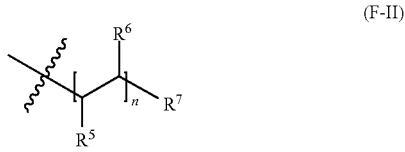
(F-II)

wherein $R^5$ and $R^6$ at each occurrence are each independently a hydrogen or a $C_1$-$C_{30}$ linear alkyl group and n is a positive integer, provided however, among all of $R^5$ and $R^6$, at least one is a $C_1$-$C_{30}$ linear alkyl group; and $R^7$ is a hydrogen or a $C_1$-$C_{30}$ linear alkyl group;
$R^3$ is hydrogen or a $C_1$-$C_{5000}$ alkyl group; and
$R^4$ is a $C_1$-$C_{50}$ alkyl group or an aromatic group.

In one embodiment, $R^3$ may be hydrogen, e.g., when a uPAO used during synthesis is a vinylidene olefin.

Alternatively, $R^3$ may be a $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{800}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or $C_1$-$C_{10}$ alkyl group. The alkyl group may be linear or branched. In particular, $R^3$ may be a $C_1$-$C_{100}$ alkyl group.

Additionally or alternatively, $R^1$ may be a linear or branched $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{500}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or a $C_1$-$C_{10}$ alkyl group.

In certain variations, $R^2$ each independently may be a $C_4$-$C_{30}$ linear alkyl group, a $C_4$-$C_{24}$ linear alkyl group, a $C_4$-$C_{20}$ linear alkyl group, a $C_4$-$C_{18}$ linear alkyl group or $C_4$-$C_{16}$ linear alkyl group.

In another embodiment, $R^1$ may be a $C_1$-$C_{100}$ linear alkyl group, a $C_1$-$C_{50}$ linear alkyl group, a $C_1$-$C_{30}$ linear alkyl group or $C_1$-$C_{10}$ linear alkyl group and $R^2$ may be a $C_4$-$C_{30}$ linear alkyl group, a $C_4$-$C_{24}$ linear alkyl group, a $C_4$-$C_{20}$ linear alkyl group, a $C_4$-$C_{18}$ linear alkyl group, a $C_4$-$C_{16}$ linear alkyl group or $C_1$-$C_{14}$ linear alkyl group.

In certain variations, $R^1$ or $R^2$ may be a $C_4$-$C_{5000}$ branched alkyl group represented by formula (F-II) above where n is larger than one (1), and at least 50% (e.g., at least 60%, 70%, 80%, 90%, or even 95%) of $R^5$ are hydrogen, and at least 50% (e.g., at least 60%, 70%, 80%, 90%, or even 95%) of $R^6$ are independently a $C_1$-$C_{30}$ linear alkyl group. In certain variations among these where a portion of $R^5$ and at least a portion of $R^6$ are alkyl groups, at least 80% of those $R^5$ that are alkyl groups are $C_1$-$C_4$ linear alkyl groups, and at least 80% of $R^6$ are $C_4$-$C_{30}$ linear alkyl groups. In certain variations, all $R^5$ are hydrogen, and all $R^6$, the same or different, are independently $C_1$-$C_{30}$ linear alkyl group. In certain variations, all $R^5$ are hydrogen, and all $R^6$ are identical $C_1$-$C_{30}$ linear alkyl groups.

In certain variations, $R^1$ or $R^2$ may be a $C_4$-$C_{5000}$ branched alkyl group represented by formula (F-II) above, and at least 50% (e.g., at least 60%, 70%, 80%, 90%, or even 95%) of $R^6$ are hydrogen, and at least 50% (e.g., at least 60%, 70%, 80%, 90%, or even 95%) of $R^5$ are independently a $C_1$-$C_{30}$ linear alkyl group. In certain variations among these where a portion of $R^6$ and at least a portion of $R^5$ are alkyl groups, at least 80% of those $R^6$ that are alkyl groups are $C_1$-$C_4$ linear alkyl groups, and at least 80% of $R^5$ are $C_4$-$C_{30}$ linear alkyl groups. In certain variations, all $R^6$ are hydrogen, and all $R^5$, the same or different, are independently $C_1$-$C_{30}$ linear alkyl group. In certain variations, all $R^6$ are hydrogen, and all $R^5$ are identical $C_1$-$C_{30}$ linear alkyl groups.

Additionally or alternatively, $R^4$ may be a $C_1$-$C_{500}$ alkyl group, a $C_1$-$C_{300}$ alkyl group, a $C_1$-$C_{100}$ alkyl group, a $C_1$-$C_{50}$ alkyl group, a $C_1$-$C_{30}$ alkyl group or $C_1$-$C_{10}$ alkyl group. The alkyl group may be linear or branched. In particular, $R^4$ may be a $C_1$-$C_{50}$ alkyl group, more particularly, a $C_1$-$C_{50}$ linear alkyl group or a $C_1$-$C_{30}$ linear alkyl group.

Additionally or alternatively, $R^4$ may be an aromatic group. Suitable aromatic groups include, but are not limited to, one or more phenyl groups, optionally substituted with one or more alkyl groups, alkoxy groups or halogens (e.g., F, Cl, Br), hydroxyl groups, nitro group, and optionally containing a heteroatom (e.g., N, O, S). For example, aromatic groups include, but are not limited to 4-methylphenyl, 4-methoxyphenyl, benzyl, 2-naphthyl, 1-naphthyl, pyridinyl, 2,3,4,5,6,-pentafluorophenyl, 2,3,5,6-tetrafluorophenyl, 2,3-dichlorophenyl, 2,4-dichlorophenyl, 2,5-dichlorophenyl, 3,4-dichlorophenyl, 3,5-dichlorophenyl, 2,4-diflurophenyl, 3,4-diflurophenyl, 2-bromophenyl, 3-bromophenyl, 4-bromophenyl, 2-chlorophenyl, 3-chlorophenyl, 4-chlorophenyl, 2-fluorophenyl, 3-fluorophenyl, 4-fluorophenyl, 2-chlorobenzyl, 4-chlorobenzyll, 3-nitrobenzyl, 4-nitrobenzyl, 2-benzeyl alcohol, 4-nitrophenyl, 2-hydroxyphenyl, 3-hydroxyphenyl, 4-hydroxyphenyl, 2-aminophenyl, 3-aminophenyl, 4-aminophenyl, 2-(trifluoromethyl)phenyl, 4-bromo-2-fluorophenyl, 4-chloro-2-fluorobenzyl, 3,4-difluorobenzyl, 3,5-difluorobenzyl, 2-bromobenzyl, 3-bromobenzyl, 4-bromobenzyl, 3-fluorobenzyl, 4-fluorobenzyl, 2-methoxyphenyl, 3-methoxyphenyl, 4-methoxyphenyl, 2-methylphenyl, 3-methylphenyl, 4-(methylsulfanyl)phenyl, 2-phenoxyethyl, 3-ethoxyphenyl, 4-methoxybenzyl, 2,5-dimethoxyphenyl, 3,4-dimethoxyphenyl, 2,4-dimethylphenyl, 2,5-dimethylphenyl, 2,6-dimethylphenyl, 1,3,5-dimethylphenyl, 2,6-dimethylphenyl, 2-ethylphenyl, 2-phenylethyl, 1,2-xylyl, 1,3-xylyl, 1,4-xylyl, 2-isopropylphenyl, 4-isopropylphenyl, 4-(dimethylamino) phenyl, 2,4,6-trimethylbenzyl, 4-tert-butylbenzyl, 4-tert-butylphenyl, tert-dodecylmercaptan, tribenzyl, 9-fluorenylmethyl, 9-fluorenyl, and the like, or combination of those.

Examples of compounds of formula (F-I) are shown below in TABLE II.

TABLE II

Exemplary Compounds of Formula (F-I)

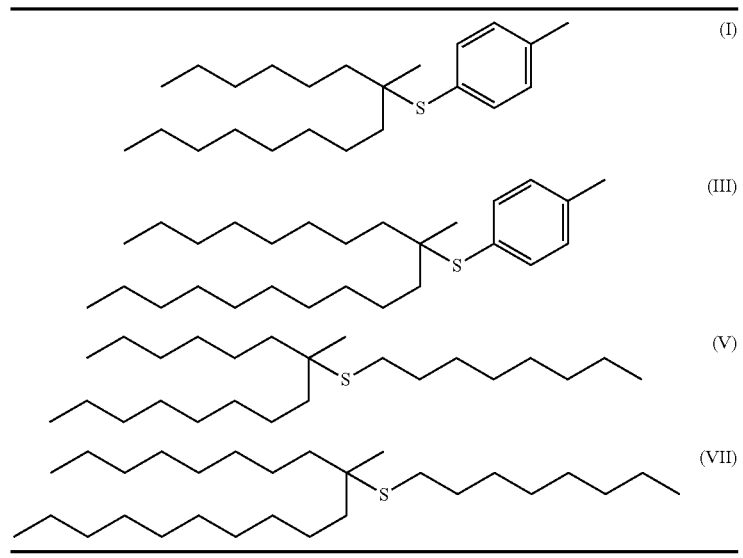

The compounds of formula (F-I) described herein may have various levels of regio-regularity. For example, each compound of formula (F-I) may be substantially atactic, isotactic, or syndiotactic. The compounds, however, can be a mixture of different molecules, each of which can be atactic, isotactic, or syndiotactic. Without intending to be bound by a particular theory, however, it is believed that regio-regular molecules, especially the isotactic ones, due to the regular distribution of the pendant groups, especially the longer ones, tend to contribute to increased performance (e.g., electrohydrodynamic lubrication performance) of base stocks comprising those compounds of formula (F-I) described herein. Thus, it is preferred that at least about 50 mol %, or at least about 60 mol %, or at least about 70 mol %, or at least about 75 mol %, or at least about 80 mol %, or at least about 90 mol %, or even about 95 mol % of the compounds of formula (F-I) described herein are regio-regular. It is further preferred that at least about 50 mol %, or at least about 60 mol %, or at least about 70 mol %, or at least about 75 mol %, or at least about 80 mol %, or at least about 90 mol %, or even about 95 mol %, of compounds of formula (F-I) described herein are isotactic.

III. Processes for Making the Sulfur-Containing Compounds

Processes for making the compounds of formula (F-I) are provided herein. In particular, the process comprises reacting HS-$R^4$ (i.e., a thiol) with an olefin-containing material comprising a compound having the following formula (F-Ia) below:

in the presence of an acid catalyst, wherein $R^1$, $R^2$, $R^3$ and $R^4$ are as described above in association with formula (F-I).

As described above, synthesis of S-PAOs according to Scheme A, under radical initiated conditions, follows the anti-Markovnikov addition, which introduce a tertiary C—H bond in addition to the sulfur atom. This tertiary C—H bond can be prone to oxidative degradation thereby lowering the oxidative stability of the S-PAO. It was unexpectedly discovered that oxidative-stability enhancing sulfur atoms may be introduced without also simultaneously introducing an oxidatively labile tertiary C—H bond via the process described herein. Indeed, compounds of formula (F-I) (S-PAOs) with increased thermal and oxidative stability may be prepared by reacting uPAOs with thiol compounds under acid catalyzed conditions so that the sulfur atom bonds to the more highly substituted carbon atom of the double bond from the uPAO oligomer.

Thus, advantageously, the process described herein has a high selectivity for producing compounds that correspond in structure to formula (F-I). For example, at least about 50 mol %, at least about 60 mol %, at least about 70 mol %, at least about 80 mol %, at least about 90 mol %, at least about 95 mol % or about 99 mol % of the compounds produced correspond in structure to formula (F-I). Additionally or alternatively, about 50 mol % to about 99 mol %, about 70 mol % to about 99 mol %, about 80 mol % to about 99 mol %, or about 90 mol % to about 99 mol % of the compounds produced correspond in structure to formula (F-I). Theoretically, even if this reaction has a lower selectivity than 90 mol %, one can nonetheless purify the product mixture to obtain a final product having higher than 90 mol % of purity of the intended product. In some instances, the balance of S-PAO compounds formed have the sulfur atom bonded to a primary or secondary carbon originating from the uPAO.

In various aspects, $R^3$ may be hydrogen. In some instances, the olefin-containing material may comprise one or more olefin compounds of formula (F-Ia), where $R^3$ is hydrogen, in an amount of at least about 1.0 wt %, at least about 10 wt %, at least about 20 wt %, at least about 30 wt %, at least about 40 wt %, at least about 50 wt %, at least about 60 wt %, at least about 70 wt %, at least about 75 wt %, at least about 80 wt %, at least about 90 wt %, at least about 99 wt %, or about 100 wt % based on the total weight of the olefin-containing material. In particular, the olefin-containing material may comprise a compound of formula (F-Ia), where $R^3$ is hydrogen, in an amount of at least about 75 wt %. Additionally or alternatively, the olefin-containing material may comprise a compound of formula (F-Ia), where $R^3$ is hydrogen, in an amount of about 1.0 wt % to about 100 wt %, of about 1.0 wt % to about 99 wt %, 1.0 wt % to about 90 wt %, about 20 wt % to about 90 wt %, about 40 wt % to about 90 wt %, about 50 wt % to about 90 wt %, about 60 wt % to about 90 wt %, about 75 wt % to about 90 wt % or about 80 wt % to about 90 wt %.

Alternatively, $R^3$ may be a $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{800}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or $C_1$-$C_{10}$ alkyl group. In some instances, the olefin-containing material may comprise one or more compounds of formula (F-Ia), where $R^3$ is an alkyl group (e.g., $C_1$-$C_{100}$ alkyl group), in an amount of at least about 1.0 wt %, at least about 10 wt %, at least about 20 wt %, at least about 25 wt %, at least about 30 wt %, at least about 40 wt %, at least about 50 wt %, at least about 60 wt %, at least about 70 wt %, at least about 75 wt %, at least about 80 wt %, at least about 90 wt %, at least about 99 wt %, or about 100 wt % based on the total weight of the olefin-containing material In particular, the olefin-containing material may comprise a compound of formula (F-Ia), where $R^3$ is an alkyl group (e.g., $C_1$-$C_{100}$ alkyl group) in an amount of at least about 50 wt %. Additionally or alternatively, the olefin-containing material may comprise a compound of formula (F-Ia), where $R^3$ is an alkyl group (e.g., $C_1$-$C_{100}$ alkyl group), in an amount of about 1.0 wt % to about 100 wt %, 1.0 wt % to about 99 wt %, 1.0 wt % to about 90 wt %, about 10 wt % to about 60 wt %, about 10 wt % to about 50 wt %, about 10 wt % to about 40 wt % or about 10 wt % to about 25 wt %.

In some embodiments, the olefin-containing material may comprise a mixture of compounds of formula (F-Ia). For example, the olefin-containing material may comprise a mixture of: (i) one or more olefin compounds of formula (F-Ia) wherein $R^3$ is hydrogen; and (ii) one or more compounds of formula (F-Ia) wherein $R^3$ is an alkyl group (e.g., $C_1$-$C_{100}$ alkyl group). In some embodiments, the olefin-containing material may comprise a mixture of: (i) about 1.0 wt % to about 99 wt % of one or more olefin compounds of formula (F-Ia) wherein $R^3$ is hydrogen; and (ii) about 1.0 wt % to about 99 wt % of one or more olefin compounds of formula (F-Ia) wherein $R^3$ is an alkyl group (e.g., $C_1$-$C_{100}$ alkyl group). In particular, the olefin-containing material may comprise a mixture of: (i) about 50 wt % to about 90 wt % or about 75 wt % to about 90 wt % of one or more olefin compounds of formula (F-Ia) wherein $R^3$ is hydrogen; and (ii) about 10 wt % to about 50 wt % or about 10 wt % to about 25 wt % of one or more olefin compounds of formula (F-Ia) wherein $R^3$ is an alkyl group (e.g., $C_1$-$C_{100}$ alkyl group).

The olefin-containing materials used in the process may be PAO (mPAO, cPAO, and mixtures thereof) dimers ($C_4$-$C_{100}$), trimers ($C_6$-$C_{100}$), tetramers ($C_8$-$C_{100}$) pentamer, hexamer, and higher oligomers, and the like, or alpha-olefins (e.g., $C_2$-$C_{30}$ alpha-olefin). Suitable alpha-olefins include, for example, alkyl olefins such as 1-hexene, 1-octene, 1-decene, 1-dodecene, 1-tetradecene, 1-octadecene, and the like.

The PAO dimer (e.g., mPAO, cPAO) can be any dimer with terminal C═C double bond prepared by using metallocene or other single-site catalyst. The dimer can be from an alpha-olefin (e.g., $C_2$-$C_{30}$ alpha-olefin), for example, 1-hexene, 1-octene, 1-decene, 1-dodecene, 1-tetradecene, 1-octadecene or a combination of alpha-olefins. In particular, the olefin-containing material in the process provided herein may be produced by oligomerization of a $C_1$-$C_{100}$ alpha-olefin in the presence of a metallocene compound. Metallocene-catalyzed alpha-olefin oligomerization processes are described in U.S. Pat. Nos. 5,688,887 and 6,043,401 and WO 2007/011973, each of which is incorporated herein by reference in its entirety and to which reference is made for details of feeds, metallocene catalysts, process conditions and characterizations of products.

In some examples, at least about 50 mol %, or at least about 60 mol %, or at least about 70 mol %, or at least about 75 mol %, or at least about 80 mol %, or at least about 90 mol %, or even about 95 mol %, of the olefin-containing materials described herein are isotactic. In particular, at least about 60 mol %, or at least about 75 mol %, or at least about 80 mol % of the olefin-containing materials described herein are isotactic.

The cPAOs may be made by using conventional catalysts to form olefin-containing material having a formula (F-Ib). Examples of suitable conventional catalysts include but are not limited to Lewis acid compounds, such as $BF_3$, $AlCl_3$, aluminum trialkyls, or combinations thereof. When using conventional catalysts, the resultant olefin-containing material tends to be a mixture of olefin compounds with highly varied $R^1$, $R^2$ and $R^3$. At least one of $R^1$, $R^2$ and $R^3$ may be an alkyl having a carbon backbone chain having multiple pendant groups attached thereto, many of which are short-chain alkyls such as methyl, ethyl, and the like. The distribution of such pendant groups on the backbone chain can be random. Such unhydrogenated cPAOs obtained by using conventional catalysts typically may be atactic. Processes for the production of cPAOs are disclosed, for example, in the following patents, each of which is incorporated herein by reference in its entirety: U.S. Pat. Nos. 3,149,178; 3,382,291; 3,742,082; 3,769,363; 3,780,128; 4,172,855; and 4,956,122; as well as in Shubkin, R. L. (Ed.) (1992) *Synthetic Lubricants and High-Performance Functional Fluids* (*Chemical Industries*) New York: Marcel Dekker Inc.

PAO lubricant compositions in which little double bond isomerization is found has resulted in different classes of high viscosity index PAO (HVI-PAO), which are also contemplated for use herein. In one class of HVI-PAO, a reduced chromium catalyst is reacted with an alpha-olefin monomer. Such PAOs are described in U.S. Pat. Nos. 4,827,073; 4,827,064; 4,967,032; 4,926,004; and 4,914,254, each of which is incorporated herein by reference in its entirety.

As described herein, $R^4$ may be an alkyl group (e.g., $C_1$-$C_{500}$ alkyl group, a $C_1$-$C_{300}$ alkyl group, a $C_1$-$C_{100}$ alkyl group, a $C_1$-$C_{50}$ alkyl group, etc.) or an aromatic group. Thus, illustrative thiols useful in the process describe herein include, for example, aliphatic thiols and aromatic thiols. Illustrative aliphatic thiols include, for example, 1-butanethiol, 1-hexanethiol, 1-octanethiol, 1-decanehiol, 1-dodecanethiol, 1-hexadecanethiol, 1-octadecanethiol, and the like. Other illustrative aliphatic thiols useful in this disclosure include, for example, methanethiol (m-mercaptan), ethanethiol (e-mercaptan), 1-propanethiol (n-P mercaptan), 2-propanethiol (2C3 mercaptan), 1-butanethiol, (n-butyl mercaptan), tert-butyl mercaptan, 1-pentane thiols (pentyl mercaptan), 1-hexanethiol, 1-heptane thiols (heptyl mercaptan), 1-octanethiol, 1-nonanethiol, 1-decanethiol, 1-dodecanethiol, 1-hexadecanethiol, 1-octadecanethiol, cyclohexanethiol, 2,4,4-trimethyl-2-pentanethiol, and the like, or combination of those.

Illustrative aromatic thiols include, for example, thiophenol, 4-methylbenzenethiol, 4-methoxythiophenol, benzyl mercaptan, 4-mercaptopyridine, 2-mercaptopyrimidine, 1-naphthalenethiol, 2-naphthalenethiol, and the like. Other illustrative aromatic thiols useful in this disclosure include, for example, 2,3,4,5,6,-pentafluorothiophenol, 2,3,5,6-tetrafluorothiophenol, 2,3-dichlorothiophenol, 2,4-dichlorothiophenol, 2,5-dichlorothiophenol, 3,4-dichlorothiophenol, 3,5-dichlorothiophenol, 2,4-diflurothiophenol, 3,4-difluorothiophenol, 2-bromothiophenol, 3-bromothiophenol, 4-bromothiophenol, 2-chlorothiophenol, 3-chlorothiophenol, 4-chlorothiophenol, 2-fluorothiophenol, 3-fluorothiophenol, 4-fluorothiophenol, 2-chlorobenzenemethanethiol, 4-chlorobenzenemethanethiol, (3-nitrobenzyl) marcaptan, (4-nitrobenzyl)marcaptan, 2-mercaptobenzeyl alcohol, 4-nitrothiophenol, 2-mercaptophenol, 3-mercaptophenol, 4-mercaptophenol, 2-aminothiophenol, 3-aminothiophenol, 4-aminothiophenol, 2-(trifluoromethyl)benzenethiol, 4-bromo-2-fluorobenzyl mercaptan, 4-chloro-2-fluorobenzyl mercaptan, 3,4-difluorobenzyl mercaptan, 3,5-difluorobenzyl mercaptan, 2-bromobenzyl mercaptan, 3-bromobenzyl mercaptan, 4-bromobenzyl mercaptan, 3-fluorobenzyl mercaptan, 4-fluorobenzyl mercaptan, 2-methoxythiophenol, 3-methoxythiophenol, 2-methylbenzenethiol, 3-methylbenzenethiol, benzylmercaptan, 4-(methylsulfanyl)thiophenol, 2-phenoxyethanethiol, 3-ethoxythiolphenol, 4-methoxy-α-toluenethiol, 2,5-dimethoxythiophenol, 3,4-dimethoxythiophenol, 2,4-dimethylthiophenol, 2,5-dimethylthiophenol, 2,6-dimethylthiophenol, 1,3,5-dimethylthiophenol, 2,6-dimethylthiophenol, 2-ethylbenzenethiol, 2-phenylethanethiol, 1,2-benzenedimethanethiol, 1,3-benzenedimethanethiol, 1,4-benzenedimethanethiol, 2-isopropylbenzenethiol, 4-isopropylbenzenethiol, 4-(dimethylamino)thiophenol, 1-naphthalenethiol, 2-naphthalenethiol, 2,4,6-trimethylbenzyl mercaptan, 4-tert-butylbenzyl mercaptan, 4-tert-butylbenzenethiol, tert-dodecylmercaptan, triphenylmethanethiol, 9-fluorenylmethylthiol, 9-mercaptofluorene, and the like, or combination of those.

Suitable acid catalysts that can be used in the processes described herein for making the compound having formula (F-I) include, for example, a Lewis acid. The Lewis acid catalysts useful for coupling reactions include metal and metalloid halides conventionally used as Friedel-Crafts catalysts. Suitable examples include $AlCl_3$, $BF_3$, $AlBr_3$, $TiCl_3$, and $TiCl_4$, either as such or with a protic promoter. Other examples include solid Lewis acid catalysts, such as synthetic or natural zeolites; acid clays; polymeric acidic resins; amorphous solid catalysts, such as silica-alumina; and heteropoly acids, such as the tungsten zirconates, tungsten molybdates, tungsten vanadates, phosphotungstates and molybdotungstovanadogermanates (e.g., $WO_x/ZrO_2$ and $WO_x/MoO_3$). Beside these catalysts, acidic ionic liquid can also be used as catalysts for coupling reactions. Among different catalysts polymeric acidic resins, such as Amberlyst 15, Amberlyst 36 are most preferred. Typically, the amount of acid catalyst used is 0.1 to 30 weight % and preferably 0.2 to 5 weight % based on total weight of the feed. In particular, the acid catalyst may be a solid acid catalyst selected from the group consisting of a solid Lewis acid, an acid clay, a polymeric acidic resin, silica-alumina, a mineral acid and a combination thereof. Examples of suitable mineral acids include, but are not limited to hydrochloric acid (HCl), hydrobromic acid (HBr), hydrofluoric acid (HF), sulfuric acid ($H_2SO_4$), phosphoric acid ($H_3PO_4$), nitric acid ($HNO_3$) and combinations thereof.

Reaction conditions for the process described herein, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 150° C. The reaction may be carried out under ambient pressure and the contact time may vary from a matter of seconds or minutes to a few hours or greater. The reactants can be added to the reaction mixture or combined in any order. The stir time employed can range from 0.5 to 48 hours, preferably from 1 to 36 hours, and more preferably from 2 to 24 hours.

In another embodiment, a compound having the formula (F-I) as described herein made by reacting HS-$R^4$ (i.e., a thiol) with an olefin-containing material comprising a compound having the following formula (F-Ia) as described herein in the presence of an acid catalyst is also provided herein.

IV. Lubricant Oil and Base Stock Compositions

This disclosure provides lubricating oils useful as engine oils and in other applications characterized by excellent stability, solvency and dispersancy characteristics. The lubricating oils are based on high quality base stocks including a major portion comprising one or more compounds corresponding in structure to formula (F-1) as described herein, also optionally, other components, such Group I, II and/or III mineral oil base stocks, GTL, Group IV (e.g., PAO), Group V (e.g., esters, alkylated aromatics, PAG) and combinations thereof. The lubricating oil base stock can be any oil boiling in the lube oil boiling range, typically between about 100 to about 450° C. In the present specification and claims, the terms base oil(s) and base stock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D 2270-93 [1998]. VI is related to kinematic viscosities measured at 40° C. and 100° C. using ASTM Method D 445-01.

IV.A. Lubricating Oil Base Stocks

A wide range of lubricating oils is known in the art. Lubricating oils that are useful in the present disclosure are both natural oils and synthetic oils. Natural and synthetic oils (or mixtures thereof) can be used unrefined, refined, or re-refined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Re-refined oils are obtained by processes analogous to refined oils but using an oil that has been previously used as a feed stock.

Groups I, II, III, IV and V are broad categories of base oil stocks developed and defined by the American Petroleum Institute (API Publication 1509; www.API.org) to create guidelines for lubricant base oils. Group I base stocks generally have a viscosity index of from 80 to 120 and contain greater than 0.03% sulfur and less than 90% saturates. Group II base stocks generally have a viscosity index of from 80 to 120, and contain less than or equal to 0.03% sulfur and greater than or equal to 90% saturates. Group III stock generally has a viscosity index greater than 120 and contains less than or equal to 0.03% sulfur and greater than 90% saturates. Group IV includes polyalpha-olefins (PAO). Group V base stocks include base stocks not included in Groups I-IV. Table III below summarizes properties of each of these five groups.

TABLE III

Base Oil Properties

| | Saturates | Sulfur | Viscosity Index |
|---|---|---|---|
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | | Includes PAO products | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked base stocks, as well as synthetic oils such as poly-alpha-olefins, alkyl aromatics and synthetic esters, i.e., Group IV and Group V oils are also well known base stock oils.

Synthetic oils include hydrocarbon oil such as polymerized and interpolymerized olefins (polybutyl ones, polypropylenes, propylene isobutylene copolymers, ethylene-olefin copolymers, and ethylene-alpha-olefin copolymers, for example). Polyalpha-olefin (PAO) oil base stocks, the Group IV API base stocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO base stocks have viscosity indices preferably greater than 130, more preferably greater than 135, still more preferably greater than 140.

In one particular embodiment, a lubricant base stock is provided. The lubricant base stock may comprise one or more of the compounds of formula (F-I) as described herein. Also contemplated herein, are formulated lubricant oil compositions comprising one or more of the lubricant base stocks described herein.

As discussed herein, the compounds of formula (F-I) unexpectedly have increased oxidative and thermal stability. Thus, compositions comprising compounds of formula (F-I), e.g., lubricant base stock compositions provided herein, may have a rotating pressure vessel oxidation test (RPVOT) break time, measured according to ASTM standard D-2272, of at least about 200 minutes, at least about 300 minutes, at least about 400 minutes, at least about 500 minutes, at least about 600 minutes, at least about 700 minutes, at least about 800 minutes, at least about 850 minutes, at least about 900 minutes or about 1000 minutes. Additionally or alternatively, compositions comprising compounds of formula (F-I), e.g., lubricant base stock compositions provided herein, may have an RPVOT break time of about 200 to about 1000 minutes, about 200 to about 900 minutes, about 300 to about 900 minutes, about 400 to about 900 minutes, about 500 to about 900 minutes, or about 400 to about 850 minutes.

Further, compositions comprising compounds of formula (F-I), e.g., lubricant base stock compositions provided herein, may have a kinematic viscosity at 100° C. (KV100), measured according to ASTM standard D-445, from about 1 to about 20 cSt, about 1 to about 15 cSt, preferably from about 2 to about 20 cSt, preferably from about 2 to about 10 cSt, and more preferably from about 2 to about 5 cSt.

Additionally or alternatively, compositions comprising compounds of formula (F-I), e.g., lubricant base stock compositions provided herein, may have a kinematic viscosity at 40° C. (KV40), measured according to ASTM standard D-445, from about 5 to about 100 cSt, preferably from about 5 to about 75 cSt, preferably from about 5 to about 500 cSt, preferably from about 5 to about 35 cSt, preferably from about 9 to about 30 cSt, and more preferably from about 9 to about 25 cSt.

Additionally or alternatively, compositions comprising compounds of formula (F-I), e.g., lubricant base stock compositions provided herein, may have a viscosity index (VI), measured according to ASTM standard D-2270, from about 5 to about 200, preferably from about 10 to about 200, preferably from about 10 to about 180, preferably from about 10 to about 150, and more preferably from about 10 to about 130.

Additionally or alternatively, compositions comprising compounds of formula (F-I), e.g., lubricant base stock compositions provided herein, may have a Noack volatility of no greater than about 35%, preferably no greater than about 30%, and more preferably no greater than about 25%. As used herein, Noack volatility is determined by ASTM D-5800.

Additionally or alternatively, compositions comprising compounds of formula (F-I), e.g., lubricant base stock compositions provided herein, may have a pour point of less than about −30° C., less than about −40° C., less than about −50° C., less than about −60° C. or −70° C. Preferably, the compositions provided herein may have a pour point of less than about −60° C. The compositions provided herein may have a pour point of about −70° C. to about −30° C., about −70° C. to about −40° C., or about −70° C. to about −50° C.

Esters in a minor amount may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols; e.g., neopentyl glycol, trimethylol ethane, 2-methyl-2-propyl-1,3-propanediol, trimethylol propane, pentaerythritol and dipentaerythritol with alkanoic acids containing at least 4 carbon atoms, preferably C5 to C30 acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in an amount such that the improved wear and corrosion resistance provided by the lubricating oils of this disclosure are not adversely affected.

Non-conventional or unconventional base stocks and/or base oils include one or a mixture of base stock(s) and/or base oil(s) derived from: (1) one or more Gas-to-Liquids (GTL) materials, as well as (2) hydrodewaxed, or hydroisomerized/cat (and/or solvent) dewaxed base stock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of 20 or greater, preferably 30 or greater and mixtures of such base stocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce tube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/followed by cat and/or solvent dewaxed wax or waxy feed, preferably F-T material derived base stock(s) and/or base oil(s), are characterized typically as having kinematic viscosities at 100° C. of from 2 mm$^2$/s to 50 mm$^2$/s (ASTM D445). They are further characterized typically as having pour points of −5° C. to −40° C. or lower (ASTM D97). They are also characterized typically as having viscosity indices of 80 to 140 or greater (ASTM D2270).

In addition, the GTL base stock(s) and/or base oils) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than 10 ppm, and more typically less than 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) and hydrodewaxed, or hydroisomerized/cat (and/or solvent) dewaxed base stock(s) and/or base oil(s) typically have very low sulfur and nitrogen content, generally containing less than 10 ppm, and more typically less than 5 ppm of each of these elements. The sulfur and nitrogen content of GTL, base stock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The base stock component of the present lubricating oils will typically be from about 50 wt % to about 99 wt % of the total composition (all proportions and percentages set out in this specification are by weight unless the contrary is stated) and more usually in the range of about 80 wt % to about 99 wt %.

IV.B. Other Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

The types and quantities of performance additives used in combination with the instant disclosure in lubricant compositions are not limited by the examples shown herein as illustrations.

IV.C. Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are from 10,000 to 1,000,000, more typically 20,000 to 500,000, and even more typically from 50,000 and 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The amount of viscosity modifier may range from zero to 8 wt %, preferably zero to 4 wt %, more preferably zero to 2 wt % based on active ingredient and depending on the specific viscosity modifier used.

IV.D. Antioxidants

Typical antioxidant include phenolic antioxidants, aminic antioxidants and oil-soluble copper complexes. Detailed description of such antioxidants and their quantities of use can be found, e.g., in WO2015/060984 A1, the relevant portions thereof are incorporated herein by reference in their entirety.

IV.E. Detergents

In addition to the alkali or alkaline earth metal salicylate detergent which is an essential component in the present disclosure, other detergents may also be present. While such other detergents can be present, it is preferred that the amount employed be such as to not interfere with the synergistic effect attributable to the presence of the salicylate. Therefore, most preferably such other detergents are not employed.

If such additional detergents are present, they can include alkali and alkaline earth metal phenates, sulfonates, carboxylates, phosphonates and mixtures thereof. These supplemental detergents can have total base number (TBN) ranging from neutral to highly overbased, i.e. TBN of 0 to over 500, preferably 2 to 400, more preferably 5 to 300, and they can be present either individually or in combination with each other in an amount in the range of from 0 to 10 wt %, preferably 0.5 to 5 wt % (active ingredient) based on the total weight of the formulated lubricating oil. As previously stated, however, it is preferred that such other detergent not be present in the formulation.

Such additional other detergents include by way of example and not limitation calcium phenates, calcium sulfonates, magnesium phenates, magnesium sulfonates and other related components (including borated detergents).

IV.F. Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenylsuccinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. Nos. 3,036,003; and 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from 1:1 to 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from 0.1 to 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N-(Z-NH-)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, leis-succinimides, and/or mixtures of mono- and bis-succinimides, wherein the hydrocarbyl succinimide is derived from a hydrocarbylene group such as polyisobutylene having a Mn of from 500 to 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of 0.1 to 20 wt %, preferably 0.1 to 8 wt %, more preferably 1 to 6 wt % (on an as-received basis) based on the weight of the total lubricant.

IV.G. Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of 0.0 to 0.5 wt %, preferably 0 to 0.3 wt %, more preferably 0.001 to 0.1 wt % on an as-received basis.

IV.H. Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of 0.01 to 0.5 wt %, preferably 0.01 to 1.5 wt %, more preferably 0.01 to 0.2 wt %, still more preferably 0.01 to 0.1 wt % (on an as-received basis) based on the total weight of the lubricating oil composition.

IV.I. Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of 0.01 to 3 wt %, preferably 0.01 to 2 wt % on an as-received basis.

IV.J. Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to 0.5 wt %, more preferably 0.001 to 0.2 wt %, still more preferably 0.0001 to 0.15 wt % (on an as-received basis) based on the total weight of the lubricating oil composition.

IV.K. Corrosion Inhibitors and Antirust Additives

Antirust additives (or corrosion inhibitors) are additives that protect lubricated metal surfaces against chemical attack by water or other contaminants. One type of antirust additive is a polar compound that wets the metal surface preferentially, protecting it with a film of oil. Another type of antirust additive absorbs water by incorporating it in a water-in-oil emulsion so that only the oil touches the surface. Yet another type of antirust additive chemically adheres to the metal to produce a non-reactive surface. Examples of suitable additives include zinc dithiophosphates, metal phenolates, basic metal sulfonates, fatty acids and amines. Such additives may be used in an amount of 0.01 to 5 wt %, preferably 0.01 to 1.5 wt % on an as-received basis.

In addition to the ZDDP anti-wear additives which are essential components of the present disclosure, other anti-wear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, diethanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 cm$^{-1}$ and an amide carbonyl band at 1620 cm$^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1 040 115 and WO 99/31113 and the molybdenum complexes described in U.S. Pat. No. 4,978,464.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

General Methods

The lube properties of the products produced in Examples 1 and 2 were evaluated as provided. The kinematic viscosity (KV) of the products was measured using ASTM standard D-445 and reported at temperatures of 100° C. (KV100) or 40° C. (KV40). The viscosity index (VI) was measured according to ASTM standard D-2270 using the measured kinematic viscosities for each product. The Noack volatility of the products was measured according to ASTM standard D-5800. The pour point of the products was measured according to ASTM D5950.

In the present and following examples, and unless otherwise stated, the C16 uPAO dimer used existed primarily (>95%) as the vinylidene olefin isomer with <5% trisubstituted or 1,2-disubstituted olefin isomers. The C16 uPAO dimer was prepared according to the methods described in International Patent Publication No. WO2007/011973, the entirety of which is incorporated herein by reference. Thus, the predominant C16 uPAO dimers would take one of the following forms:

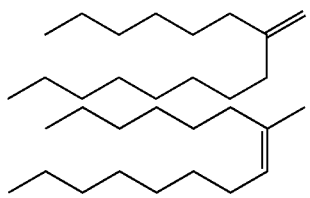

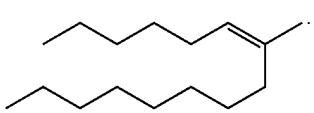

In the present and following examples, unless otherwise stated, the C20 uPAO dimer used was an approximate mixture of vinylidenes and trisubstituted olefins at a weight ratio of vinylidenes to trisubstituted olefins in the range from 20/80 to 60/40. The C20 uPAO dimer was prepared according to the method described in Example 1 of U.S. Patent Publication No. 2013/0090277 A1, the entirety of which is incorporated herein by reference. Thus, the C20 uPAO dimers would take the following predominant forms:

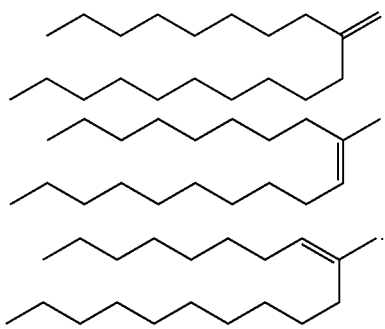

Example 1—Acid Catalyzed Synthesis of Product I Containing Compound-I and Compound-II A C16 uPAO dimer was alkylated with 4-methylbenzenethiol by acid catalyst as shown below in Scheme 1 to form Product I containing Compound-I and Compound-II.

Scheme 1

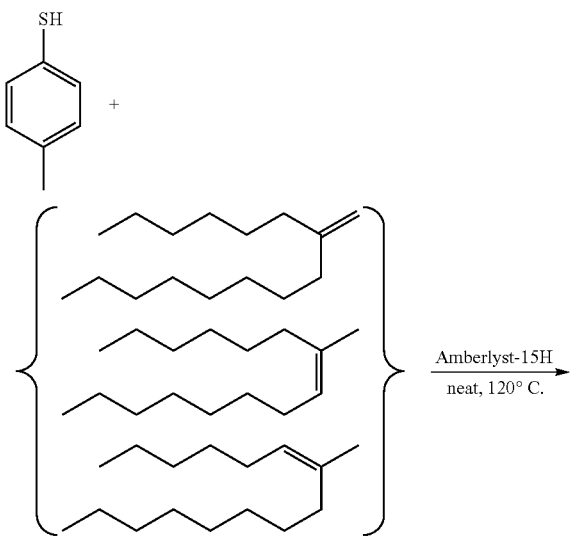

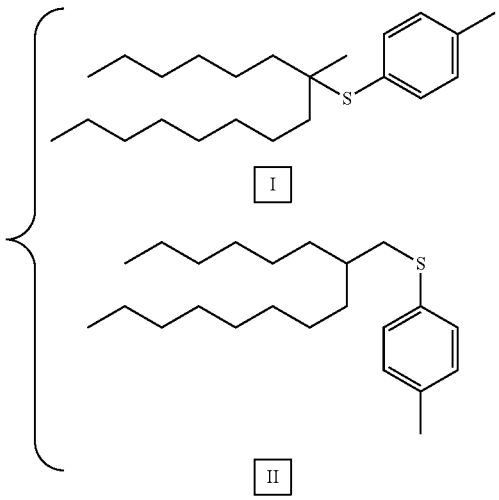

A glass reactor under $N_2$ atmosphere was charged with C16 uPAO dimer (242.1 g, 1.07 mol), 4-methylbenzenethiol (160.4 g, 1.29 mol) (obtained from Sigma-Aldrich), and Amberlyst-15H (6.89 g, 1.7 wt %) (obtained from Sigma-Aldrich) to form a mixture. The mixture was heated with stirring at 120° C. for 20 hours. The mixture was filtered to remove catalyst. The filtrate was distilled under vacuum to 160° C.-205° C. to remove unreacted olefin and thiol. The distillation pot bottoms were collected as Product I containing Compound-I and Compound-II in a molar ratio of approximately 97.5 to 2.5. The lube properties of Product I were determined as provided above and are shown below in TABLE IV.

TABLE IV

| Lube Properties | |
| --- | --- |
| KV100 (cSt) | 3.151 |
| KV40 (cSt) | 16.40 |
| VI | 11 |
| Noack volatility (%) | 21.56 |
| HPDSC | 249.61 |

Example 2—Comparative Radical Synthesis of Comparative Product 1 Containing Compound-I and Compound-II A C16 uPAO dimer was alkylated with 4-methylbenzenethiol by radical initiator as shown below in Scheme A to form Comparative Product 1 containing Compound-I and Compound-II.

Scheme A

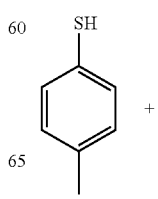

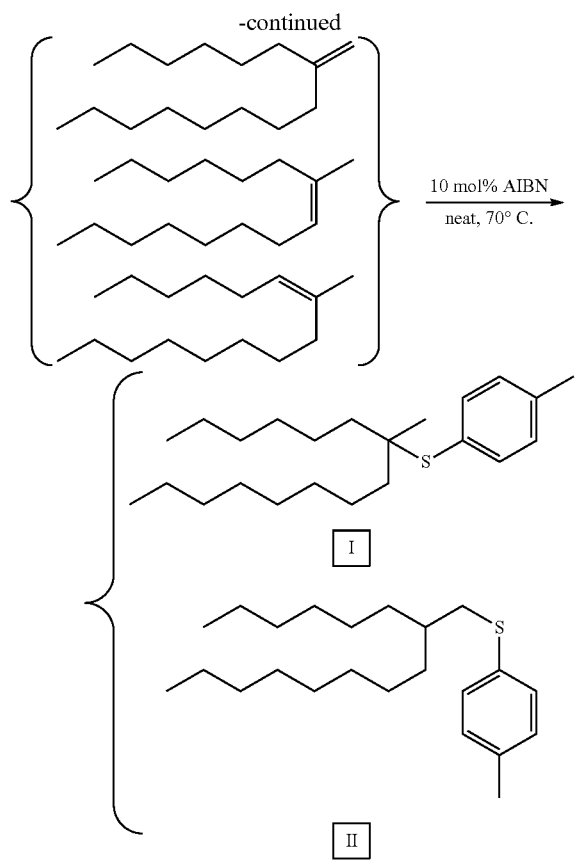

A glass reactor under $N_2$ atmosphere was charged with C16 uPAO dimer (325.0 g, 1.44 mol), 4-methylbenzenethiol (309.0 g, 2.49 mol) (obtained from Sigma-Aldrich) and AIBN (23.1 g, 0.17 mol) to form a mixture. The reactor contents were heated with stirring at 70° C. for 18 hours. The reaction mixture was put under vacuum and stripped to 185° C. to remove unreacted olefin and thiol. The distillation pot bottoms were treated with decolorizing carbon and filtered. The filtrate was collected as Comparative Product 1 containing Compound-I and Compound-II in a molar ratio of approximately 1:99 of I: II. The lube properties of Comparative Product 1 were determined as provided above and are shown below in TABLE V.

TABLE V

| Lube Properties | |
| --- | --- |
| KV100 (cSt) | 2.36 |
| KV40 (cSt) | 8.61 |
| VI | 86 |
| Pour Point (° C.) | −78 |
| Noack volatility (%) | 15.08 |
| HPDSC | 246.37 |

Product I and Comparative Product 1 contain the same types of isomers of the alkylated thiols, but at different proportions thereof. The nature of the catalyst and process conditions employed can control the regiochemistry of the sulfur addition to the double bond. This difference in molecular structure can be identified by $^1H$ and $^{13}C$ NMR.

Figure 2:
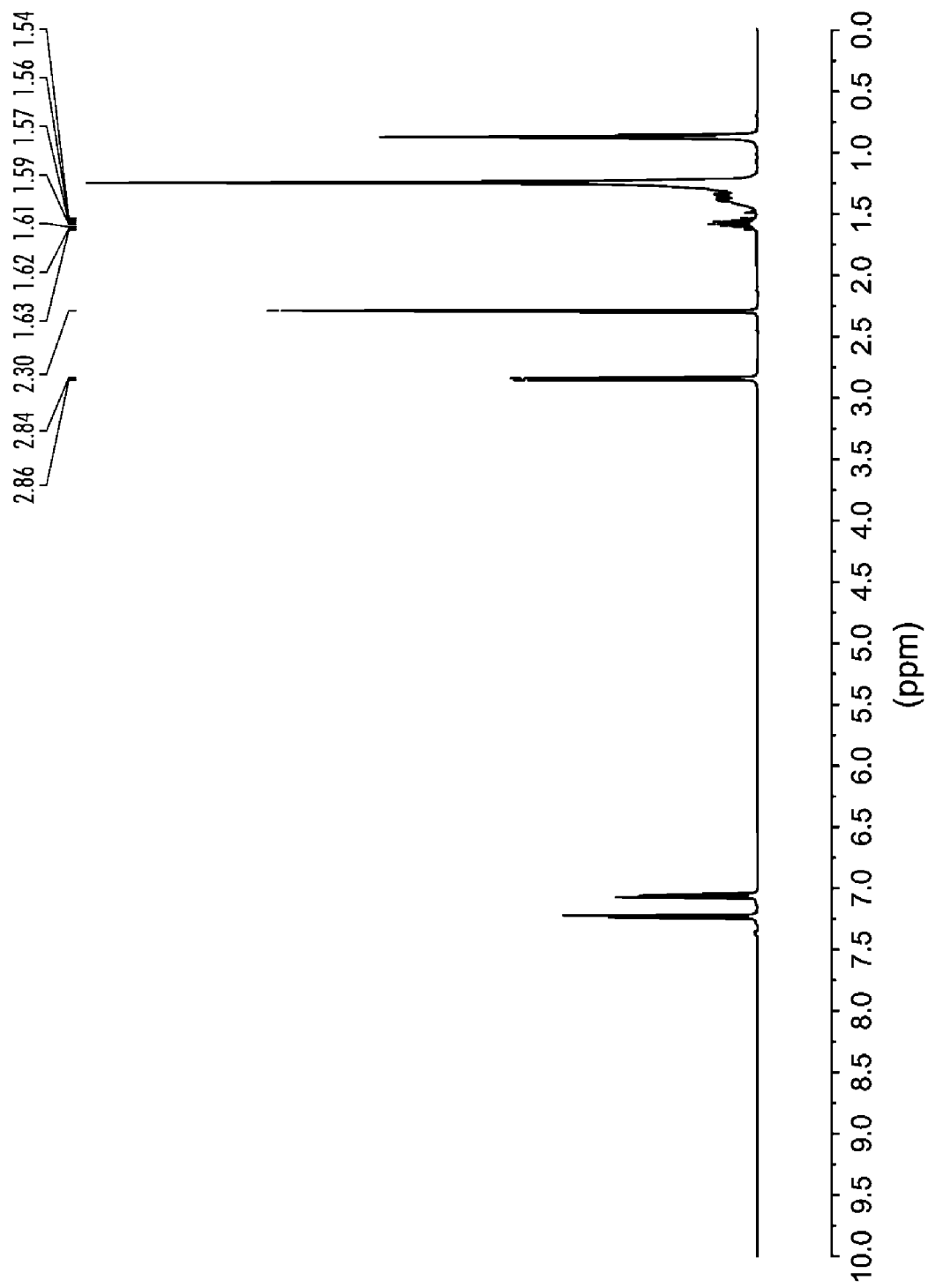
FIG. 2 illustrates $^1$H NMR spectra of Comparative Product 1.
Figure 3:
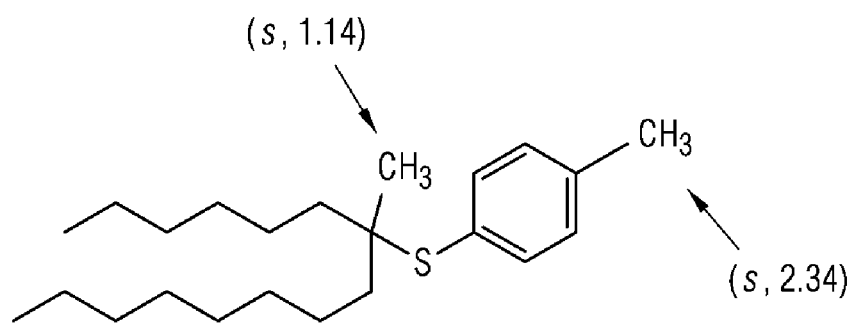
FIG. 3 illustrates $^1$H NMR structural assignment of Compound-I and Compound-II.
Figure 3:
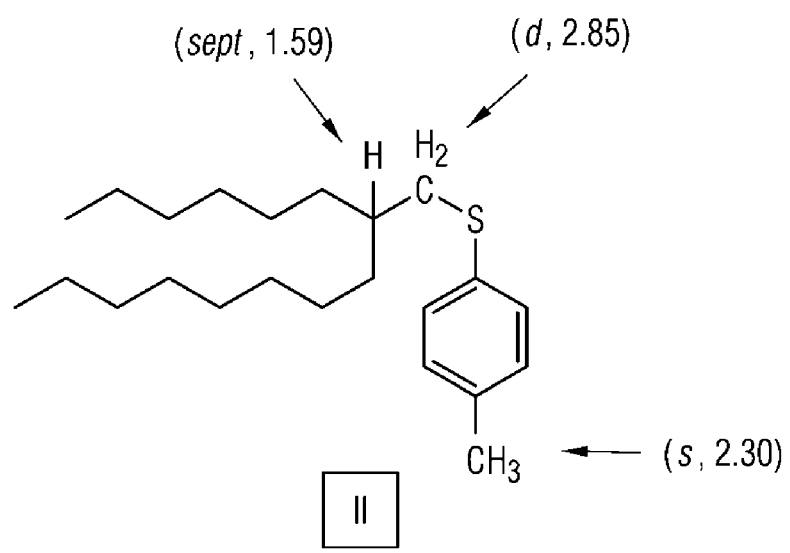

There are a few key structural features that are identifiable by $^1H$ NMR that can be used to distinguish the structure of the products. The $^1H$ NMR spectra of Product I and Comparative Product 1 were determined and are shown in FIGS. 1 and 2, respectively. Further, the $^1H$ NMR structural assignments of Compound-I and Compound-II are shown in FIG. 3. As shown, in FIG. 3, the molecular structure of Compound-I includes a methyl group positioned adjacent to the aliphatic C—S bond. The methyl group was identifiable as a singlet peak with a chemical shift of 1.14 ppm. The carbon atom of the aliphatic C—S bond has no hydrogen atoms and was thus featureless by $^1H$ NMR.

By contrast, the molecular structure of Compound-II includes a methylene group bonded to the sulfur atom. This was identifiable as a doublet peak with a chemical shift of 2.85 ppm. The carbon atom adjacent to this methylene group possesses one hydrogen atom which was identifiable as a septet peak with a chemical shift of 1.59 ppm.

The presence or absence of any of these $^1H$ NMR peaks can be used to determine whether the structure of the products or base stocks includes a sulfur atom bonded to a tertiary carbon (i.e., Compound-I) or primary carbon of the PAO moiety (i.e., Compound-II). These identifiable markers can be used to determine the molecular structure of the base stock and quantify relative amounts of different molecular isomers should a blend of isomers exist.

For example, the $^1H$ NMR spectra of Product I shown in FIG. 1 shows the singlet peak at 1.14 ppm, indicating the presence of Compound-I. It also shows a small doublet peak at 2.85 ppm, indicating the presence of a small amount of Compound-II. Normalized integration values show that the Compound-I to Compound-II molar ratio in this product was approximately 97.7 to 2.5.

On the other hand, the $^1H$ NMR spectra of Comparative Product 1 shown in FIG. 2 shows the doublet at 2.85 ppm and the septet at 1.59 ppm that is characteristic of Compound-II. However, no identifiable singlet peak exists at 1.14 ppm, indicating that the composition of Comparative Product I was nearly quantitatively (>99%) Compound-II.

Example 3—Acid Catalyzed Synthesis of Product II Containing Compound-III and Compound-IV A C20 uPAO dimer was alkylated with 4-methylbenzenethiol (obtained from Sigma-Aldrich) by acid catalyst as shown below in Scheme 2 to form Product II containing Compound-III and Compound-IV.

Scheme 2

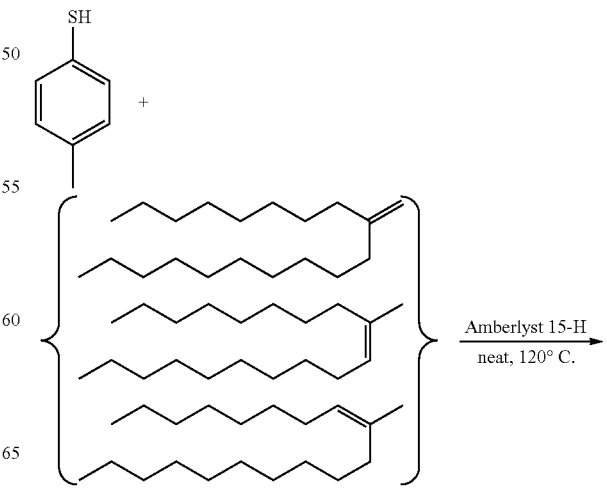

-continued

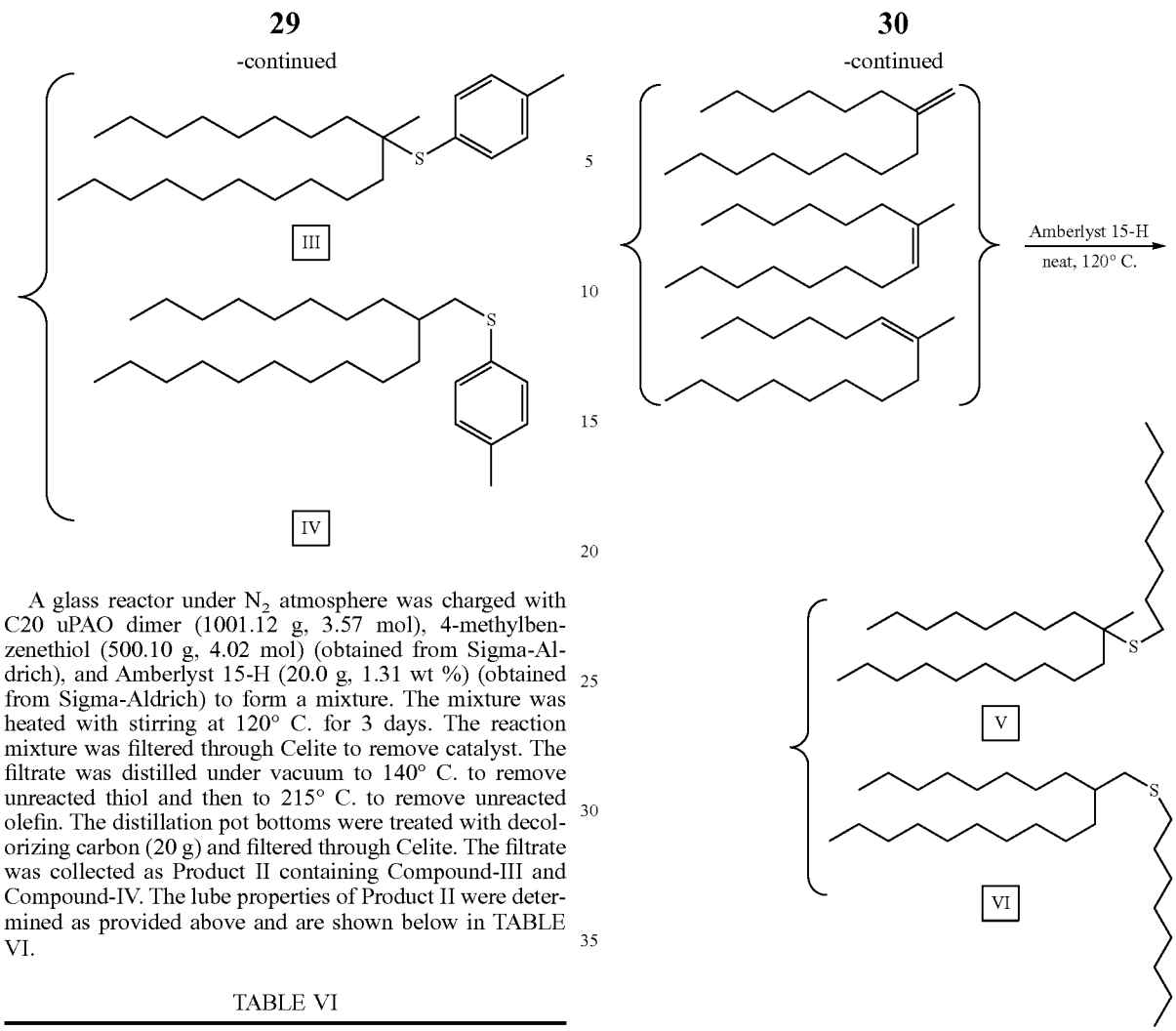

A glass reactor under $N_2$ atmosphere was charged with C20 uPAO dimer (1001.12 g, 3.57 mol), 4-methylbenzenethiol (500.10 g, 4.02 mol) (obtained from Sigma-Aldrich), and Amberlyst 15-H (20.0 g, 1.31 wt %) (obtained from Sigma-Aldrich) to form a mixture. The mixture was heated with stirring at 120° C. for 3 days. The reaction mixture was filtered through Celite to remove catalyst. The filtrate was distilled under vacuum to 140° C. to remove unreacted thiol and then to 215° C. to remove unreacted olefin. The distillation pot bottoms were treated with decolorizing carbon (20 g) and filtered through Celite. The filtrate was collected as Product II containing Compound-III and Compound-IV. The lube properties of Product II were determined as provided above and are shown below in TABLE VI.

TABLE VI

| Lube Properties | |
|---|---|
| KV100 (cSt) | 4.16 |
| KV40 (cSt) | 23.27 |
| VI | 63 |
| Pour Point (° C.) | −61 |

Example 4—Acid Catalyzed Synthesis of Product III Containing Compound-V and Compound-VI A C16 uPAO dimer was alkylated with 1-octanethiol by acid catalyst as shown below in Scheme 3 to form Product III containing Compound-V and Compound-VI.

Scheme 3

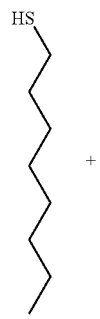

+

A glass reactor under $N_2$ atmosphere was charged with C16 uPAO dimer (200.0 g, 0.89 mol), 1-octanethiol (157.0 g, 1.07 mol) (obtained from Sigma-Aldrich), and Amberlyst-15H (10.0 g, 2.7 wt %) (obtained from Sigma-Aldrich) to form a mixture. The mixture was heated to 120° C. for 20 hours. The mixture was filtered through Celite to remove catalyst. The filtrate was distilled under vacuum to 220° C. to remove unreacted thiol and olefin. The distillation pot bottoms were treated with decolorizing carbon and filtered through Celite. The filtrate was collected as Product III containing Compound-V and Compound-VI in a molar ratio of approximately 78:22 of V:VI. The lube properties of Product III were determined as provided above and are shown below in TABLE VII.

TABLE VII

| Lube Properties | |
|---|---|
| KV100 (cSt) | 2.68 |
| KV40 (cSt) | 9.96 |
| VI | 106 |
| Noack volatility (%) | 21.01 |

Example 5—Acid Catalyzed Synthesis of Product IV Containing Compound-VII and Compound-VIII A C20 uPAO dimer was alkylated with 1-octanethiol by acid catalyst as shown below in Scheme 4 to form Product IV containing Compound-VII and Compound-VIII.

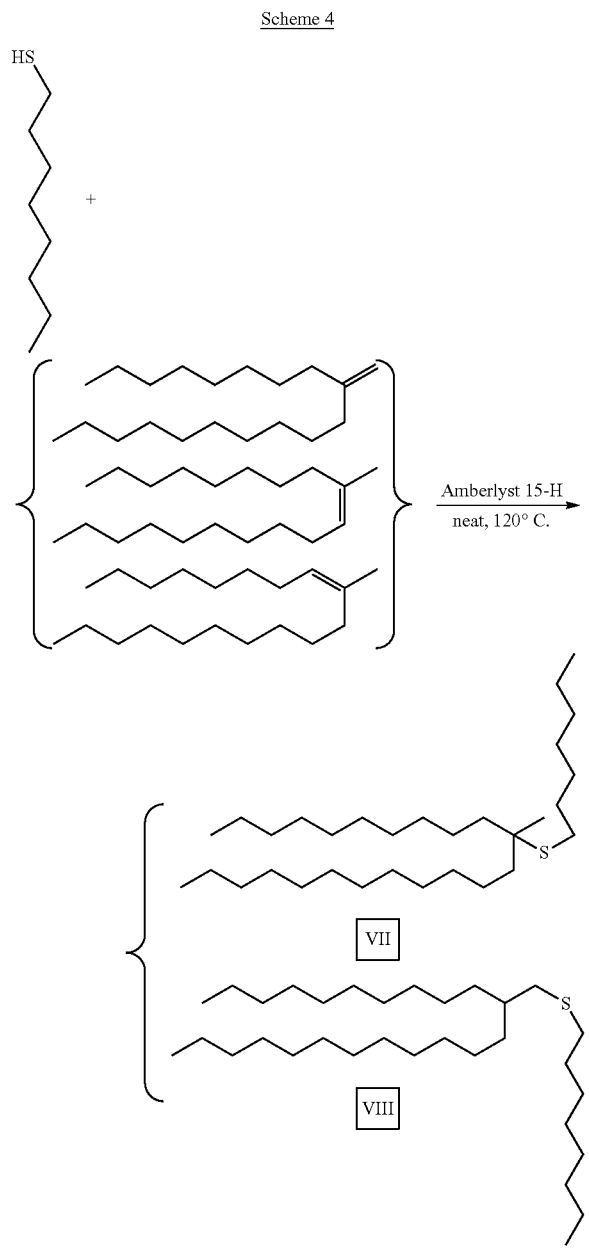

Scheme 4

A glass reactor under $N_2$ atmosphere was charge with C20 uPAO dimer (887.1 g, 3.16 mol), 1-octanethiol (554.3 g, 3.79 mol) (obtained from Sigma-Aldrich), and Amberlyst-15H (30.1 g, 3.3 wt %) (obtained from Sigma-Aldrich) to form a mixture. The mixture was heated to 120° C. for 20 hours. Additional Amberlyst-15H (15.0 g, 1.6 wt %) was added and the reaction continued for 8 hours. The mixture was filtered through Celite to remove catalyst. The filtrate was distilled under vacuum to 100° C. to remove unreacted thiol and then to 250° C. to remove unreacted olefin. The distillation pot bottoms were treated with decolorizing carbon (20 g) and filtered through Celite. The filtrate was collected as Product IV containing compounds VII and VIII in a molar ratio of approximately 95:5 of VII:VIII. The lube properties of Product IV were determined as provided above and are shown below in TABLE VIII.

TABLE VIII

| Lube Properties | |
| --- | --- |
| KV100 (cSt) | 3.58 |
| KV40 (cSt) | 14.73 |
| VI | 128 |
| Pour Point (° C.) | −69 |
| Noack volatility (%) | 7.26 |

Figure 4:
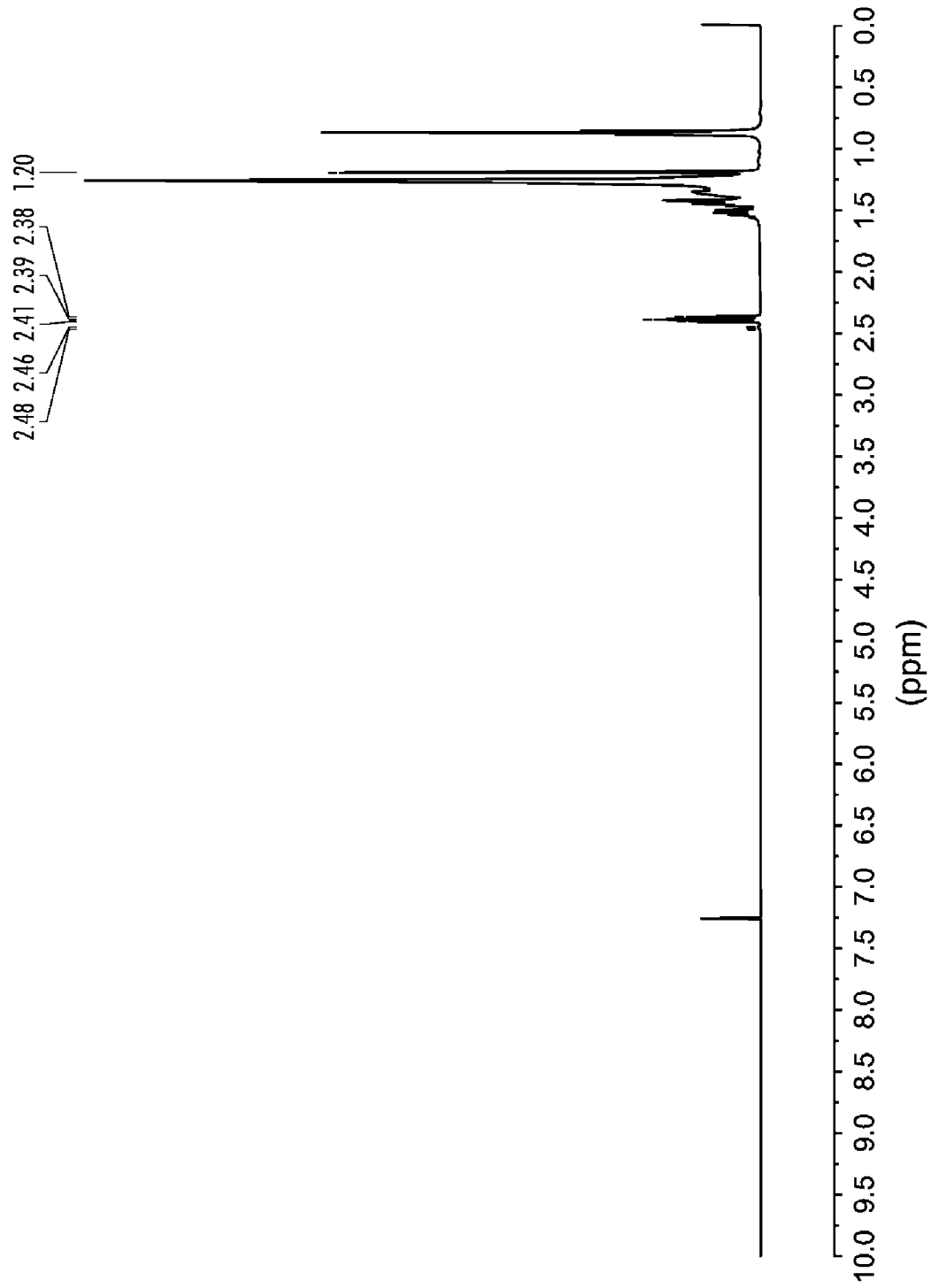
FIG. 4 illustrates $^1$H NMR spectra of Product IV.
Figure 5:
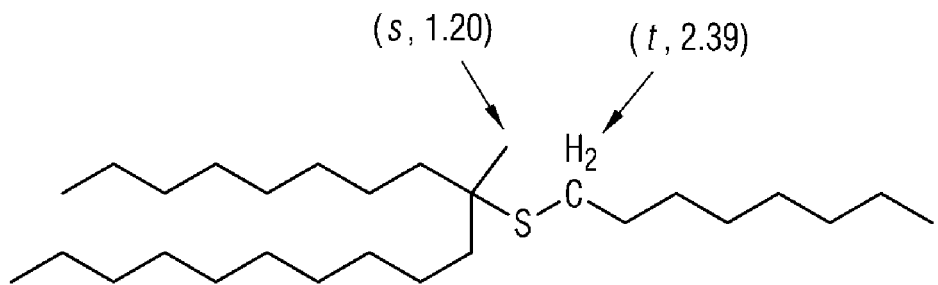
FIG. 5 $^1$H NMR structural assignment of compounds VII and VIII.
Figure 5:
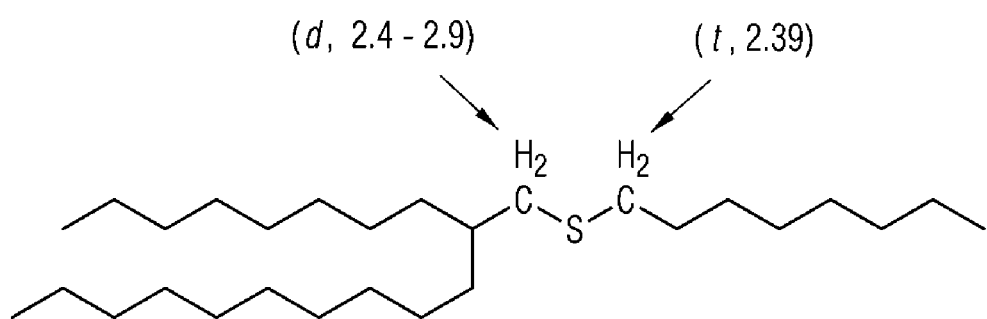

The $^1$H NMR spectra of Product IV was determined and is shown in FIG. 4. Further, the $^1$H NMR structural assignments of compounds VII and VIII are shown in FIG. 5. As shown, in FIG. 5, the molecular structure of compound VII includes a methyl group positioned adjacent to the aliphatic C—S bond. The methyl group was identifiable as a singlet peak with a chemical shift of 1.20 ppm. The carbon atom of the aliphatic C—S bond from the PAO moiety has no hydrogen atoms and was thus featureless by $^1$H NMR. The carbon atom of the aliphatic C—S bond from the aliphatic thiol moiety has two hydrogen atoms which were recognizable as a triplet peak with a chemical shift of 2.39 ppm.

Those practiced in the art will recognize that that compound VIII would also give a triplet peak at approximately 2.39 ppm, but also an additional doublet peak in the range of 2.4 to 2.9 ppm. The presence or absence of this additional doublet peak was used to quantify the relative amounts of different molecular isomers should a blend of isomers exist.

For instance, in the $^1$H NMR spectra of Product IV in FIG. 4, a triplet peak was observed at 2.39 ppm which could indicate either compound VII or VIII. However, only a minor corresponding doublet peak in the range of 2.4-2.9 ppm was observed. This, along with the observance of the strong singlet peak at 1.40 ppm, indicated that the primary structure in Product IV was compound VII, namely, the result of a Markovnikov addition of an aliphatic thiol to the uPAO dimer. Normalization of the $^1$H NMR peaks indicated that Product IV existed with a molar ratio of 95:5 of Compound-VII to Compound-VIII.

Example 6—Oxidative Stability Study

Figure 6:
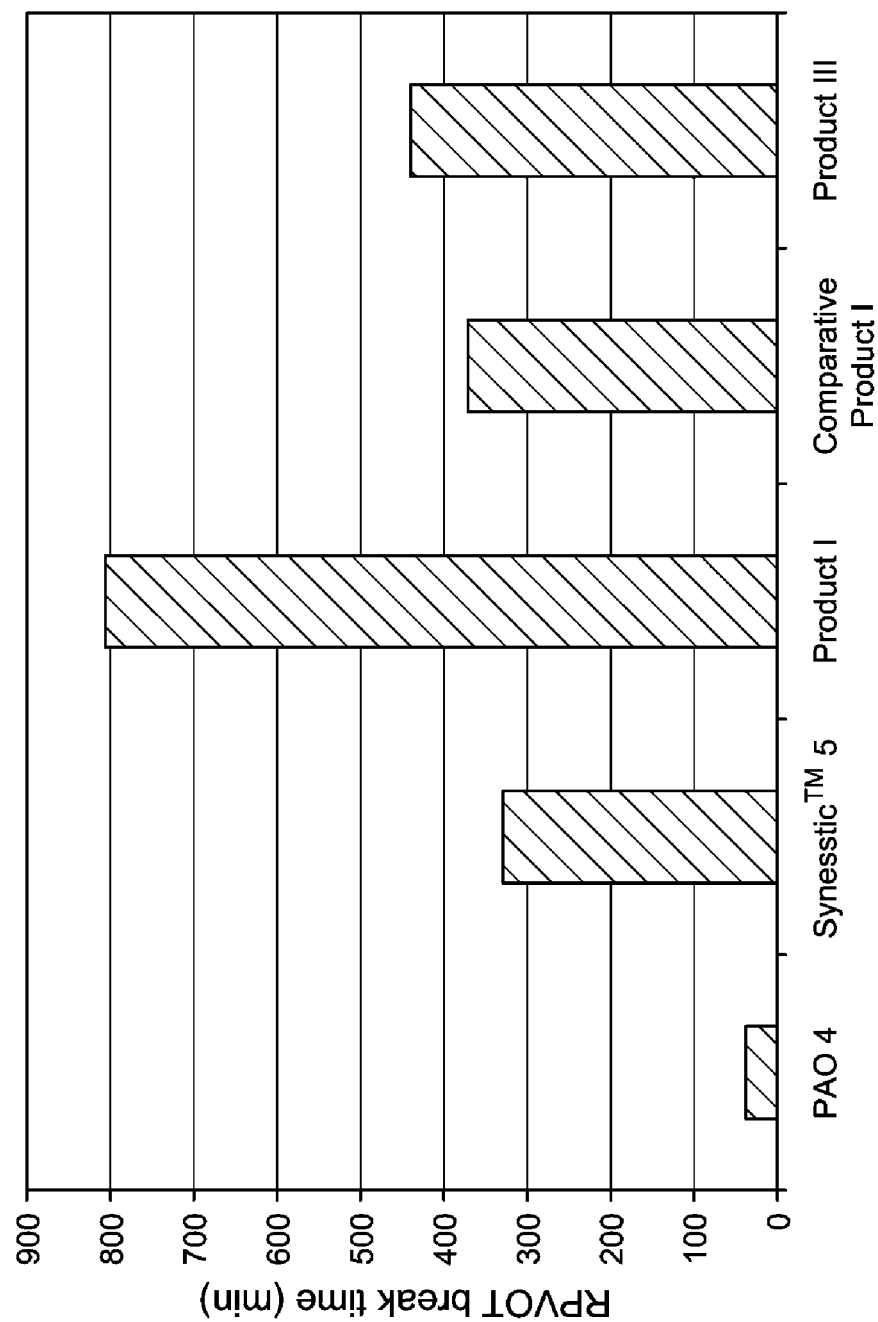
FIG. 6 illustrates oxidative stability of Product I, Product III, Comparative Product 1, PAO 4 and Synesstic™ 5.

The oxidative stability of Product I and Product III was compared against Comparative Product 1 and conventional hydrocarbon synthetic base stocks according to the methods described in ASTM D2272. The conventional hydrocarbon synthetic base stocks tested were PAO 4 and Synesstic™ 5 (both available from ExxonMobil Chemical Company, 27111 Springwoods Village Parkway, Spring, Tex. 77389, U.S.A.). The rotating pressure vessel oxidation test (RPVOT) break time of each product tested is provided in FIG. 6. Aromatic moieties tend to lend enhanced oxidative stability to a base stock molecule. Hence, the aromatic-containing Synesstic™ 5 has a longer RPVOT break time than the aliphatic PAO 4 base stock. Notably, both S-containing aromatic base stocks from Product I and Comparative Product 1 have even longer RPVOT break times than Synesstic™ 5, demonstrating that the S atom can contribute additional oxidative stability to an aromatic-containing base stock. Further, the presence of sulfur atom in an otherwise aliphatic base stock molecule can improve oxidative stability. For instance, the base stock of Product III has a longer RPVOT break time compared to a hydrocarbon base stock, such as PAO 4.

The RPVOT break time of the base stock of Product I is substantially longer than the base stock of Comparative Product 1, demonstrating that the regiochemistry of the sulfur addition and the position of the sulfur atom can strongly influence oxidative stability. The base stock of Product I, derived primarily from a Markovnikov addition of sulfur to the PAO olefin, has enhanced oxidative stability over the base stock of Comparative Product 1.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A lubricant base stock comprising a composition comprising at least 50 mol % of a compound having the formula (F-I) below:

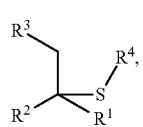

(F-I)

wherein:
$R^1$ is a $C_1$-$C_{500}$ alkyl group;
$R^2$ is (i) a $C_4$-$C_{30}$ linear alkyl group or (ii) a $C_4$-$C_{500}$ branched alkyl group having the formula (F-II) below:

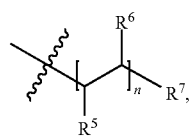

(F-II)

wherein: $R^5$ and $R^6$ at each occurrence are each independently a hydrogen or a $C_1$-$C_{30}$ linear alkyl group and n is a positive integer, provided however, among all of $R^5$ and $R^6$, at least one is a $C_1$-$C_{30}$ linear alkyl group; and $R^7$ is a hydrogen or a $C_1$-$C_{30}$ linear alkyl group;
$R^3$ is hydrogen or a $C_1$-$C_{500}$ alkyl group;
$R^4$ is a $C_1$-$C_{50}$ alkyl group or an aromatic group; and
wherein the lubricant base stock has a rotating pressure vessel oxidation test (RPVOT) break time of at least about 400 minutes,
wherein the compound is produced by a process with a selectivity for producing compounds that correspond in structure to formula (F-I) of at least about 90 mol %; and the compound has a viscosity index of about 10 to about 140.

2. The lubricant base stock of claim 1, wherein $R^3$ is hydrogen.

3. The lubricant base stock of claim 1, wherein $R^3$ is a $C_1$-$C_{100}$ alkyl group.

4. The lubricant base stock of claim 1, wherein $R^1$ is a $C_1$-$C_{30}$ linear alkyl group.

5. The lubricant base stock of claim 1, wherein:
$R^2$ is a $C_4$-$C_{30}$ linear alkyl group.

6. The lubricant base stock of claim 1, wherein:
$R^2$ is a branched alkyl group represented by formula (F-II), and one of the following conditions is met:
(i) at least 50% of $R^5$ are hydrogen, and at least 50% of $R^6$ are independently a $C_1$-$C_{30}$ linear alkyl group; and
(ii) at least 50% of $R^5$ are independently a $C_1$-$C_{30}$ linear alkyl group, and at least 50% of $R^6$ are hydrogen.

7. The lubricant base stock of claim 1, wherein among all $R^5$ and $R^6$, at least 50% by mole are independently $C_4$-$C_{30}$ linear alkyl groups.

8. The lubricant base stock of claim 1, wherein n is from 50 to 500.

9. The lubricant base stock of claim 1, wherein n is from 2 to 50.

10. The lubricant base stock of claim 1, wherein $R^1$ and $R^2$ are the same or different and are each independently a $C_4$-$C_{100}$ linear alkyl group.

11. The lubricant base stock of claim 1, wherein $R^1$ and $R^2$ are the same or different and are each independently a $C_4$-$C_{30}$ linear alkyl group.

12. The lubricant base stock of claim 1, wherein $R^4$ is a $C_1$-$C_{50}$ linear alkyl.

13. The lubricant base stock of claim 1, wherein $R^4$ is an aromatic group.

14. The lubricant base stock of claim 6, having an isotacticity of at least about 60 mol %.

15. The lubricant base stock of claim 1 which has a rotating pressure vessel oxidation test (RPVOT) break time of at least about 500 minutes.

16. A process for making a lubricant base stocks of claim 1, the process comprising:
reacting HS-$R^4$ with an olefin-containing material comprising a compound having the following formula (F-Ia) below:

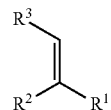

(F-Ia)

in the presence of an acid catalyst;
wherein at least about 90 mol % of the compounds produced correspond in structure to formula (F-I) of claim 1; and the compound of formula (F-I) of claim 1 has a viscosity index of about 10 to about 140.

17. The process of claim 16, wherein the olefin comprises at least about 75 wt % of the compound of formula (F-Ia) where $R^3$ is hydrogen.

18. The process of claim 16, wherein the olefin comprises at least about 50 wt % of the compound of formula (F-Ia) where $R^3$ is a $C_1$-$C_{100}$ alkyl group.

19. The process of claim 16, wherein the olefin comprises a mixture of: (i) about 50-90 wt % of the compound of formula (F-Ia) where $R^3$ is hydrogen; and (ii) about 10-50 wt % of the compound of formula (F-Ia) where $R^3$ is a $C_1$-$C_{100}$ alkyl group.

20. The process of claim 16, wherein the olefin-containing material is produced by oligomerization of a $C_1$-$C_{100}$ alpha-olefin in the presence of a metallocene compound.

21. The process of claim 20, wherein the olefin-containing material has an isotacticity of at least about 60 mol %.

22. The process of claim 16, wherein the acid catalyst is selected from the group consisting of a Lewis acid, an acid clay, a polymeric acidic resin, a heteropoly acid, an acidic ionic liquid and a combination thereof.

23. A formulated lubricant composition comprising the lubricant base stock of claim 1.

24. The formulated lubricant composition of claim 23, wherein the lubricant base stock is present in an amount from about 5 wt % to about 99 wt %.

25. The lubricant base stock of claim 1 comprising a composition comprising at least 70 mol % of formula F-I.

26. The lubricant base stock of claim 1 comprising a composition comprising at least 90 mol % of formula F-I.

27. The lubricant base stock of claim 1 comprising a composition comprising at least 95 mol % of formula F-I.

28. The lubricant base stock of claim 1 comprising a composition comprising at least 99 mol % of formula F-I.

29. The lubricant base stock of claim 1 comprising a RPVOT break time of at least about 600 minutes.

30. The lubricant base stock of claim 1 comprising a RPVOT break time of at least about 700 minutes.

* * * * *